United States Patent
Morrell et al.

(10) Patent No.: US 11,714,848 B2
(45) Date of Patent: Aug. 1, 2023

(54) TIME-BASED CLUSTER IMAGING OF AMPLIFIED CONTIGUITY-PRESERVED LIBRARY FRAGMENTS OF GENOMIC DNA

(71) Applicant: ILLUMINA CAMBRIDGE LIMITED, Cambridge (GB)

(72) Inventors: Natalie Morrell, Cambridge (GB); Andrew Slatter, Cambridge (GB); Vicki Thomson, Cambridge (GB)

(73) Assignee: Illumina Cambridge Limited, Cambridge (GB)

( * ) Notice: Subject to any disclaimer, the term of this patent is extended or adjusted under 35 U.S.C. 154(b) by 0 days.

(21) Appl. No.: 17/600,499

(22) PCT Filed: Dec. 1, 2020

(86) PCT No.: PCT/EP2020/084157
§ 371 (c)(1),
(2) Date: Sep. 30, 2021

(87) PCT Pub. No.: WO2021/110695
PCT Pub. Date: Jun. 10, 2021

(65) Prior Publication Data
US 2022/0171802 A1    Jun. 2, 2022

Related U.S. Application Data

(60) Provisional application No. 62/942,563, filed on Dec. 2, 2019.

(51) Int. Cl.
| | | |
|---|---|---|
| G06F 16/58 | (2019.01) | |
| G06V 10/26 | (2022.01) | |
| B01L 3/00 | (2006.01) | |
| B01L 7/00 | (2006.01) | |
| C12Q 1/6844 | (2018.01) | |
| G06T 5/50 | (2006.01) | |
| C12Q 1/6855 | (2018.01) | |
| C12Q 1/6853 | (2018.01) | |

(52) U.S. Cl.
CPC ........ *G06F 16/58* (2019.01); *B01L 3/502761* (2013.01); *B01L 7/52* (2013.01); *C12Q 1/6844* (2013.01); *G06T 5/50* (2013.01); *G06V 10/26* (2022.01); *B01L 2300/0816* (2013.01); *B01L 2300/0819* (2013.01); *B01L 2300/0877* (2013.01); *B01L 2300/0893* (2013.01); *C12Q 1/6853* (2013.01); *C12Q 1/6855* (2013.01); *C12Q 2304/10* (2013.01); *C12Q 2304/12* (2013.01); *C12Q 2304/13* (2013.01)

(58) Field of Classification Search
None
See application file for complete search history.

(56) References Cited

U.S. PATENT DOCUMENTS

| 8,241,573 B2 | 8/2012 | Banerjee et al. |
| 2017/0292147 A1 | 10/2017 | Kostem et al. |

OTHER PUBLICATIONS

Amini, Sasan et al, "Haplotype-resolved whole-genome sequencing by contiguity-preserving transposition and combinatorial indexing", Nature Genetics vol. 46, No. 12, pp. 1343-1349, Oct. 19, 2014.

*Primary Examiner* — G Steven Vanni
(74) *Attorney, Agent, or Firm* — Dierker & Kavanaugh, P.C.

(57) ABSTRACT

In an example method, a series of time-based clustering images is generated for a plurality of library fragments from a genome sample. Each time-based clustering image in the series is sequentially generated. To generate each time-based clustering image in the series: i) a respective sample is introduced to a flow cell, the respective sample including contiguity preserved library fragments of the plurality of library fragments, wherein the contiguity preserved library fragments are attached to a solid support or are attached to each other; ii) the contiguity preserved library fragments are released from the solid support or from each other; iii) the contiguity preserved library fragments are amplified to generate a plurality of respective template strands; iv) the respective template strands are stained; and v) the respective template strands are imaged.

27 Claims, 13 Drawing Sheets

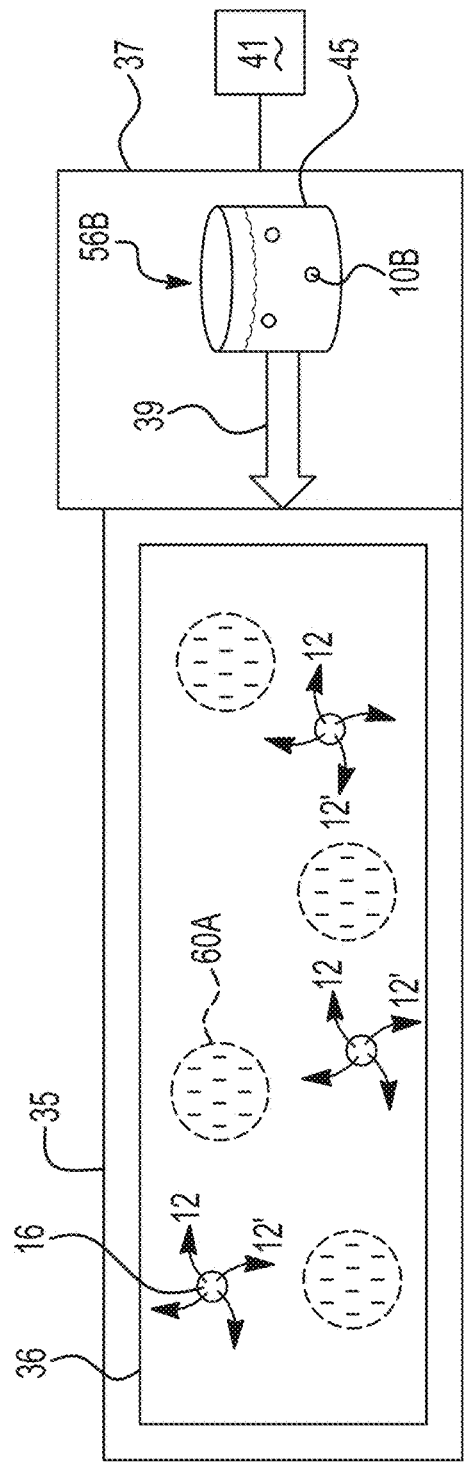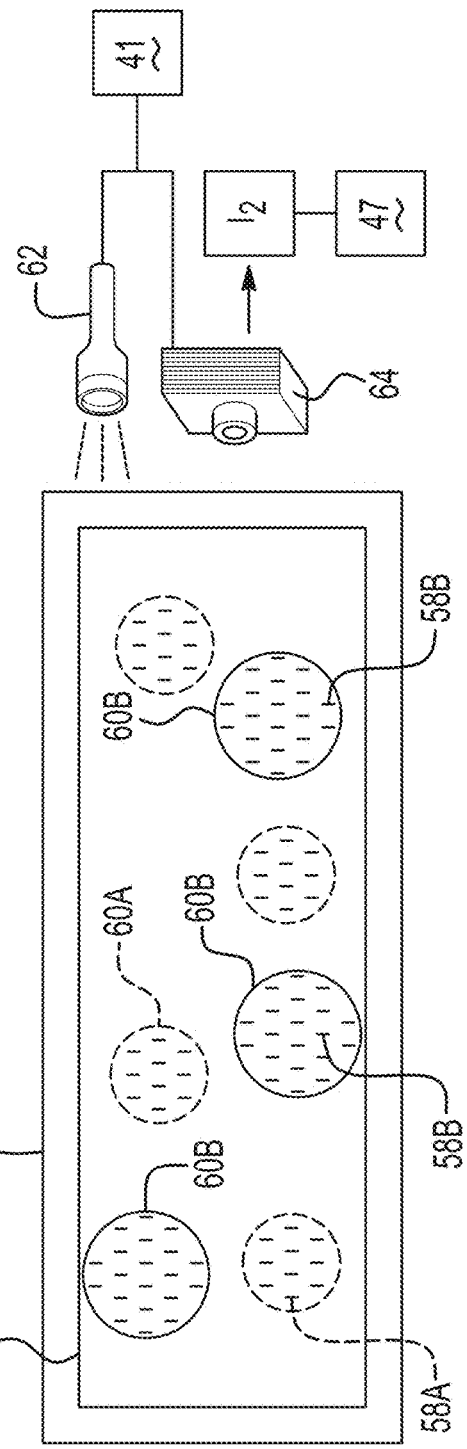

TIME-BASED CLUSTER IMAGING OF AMPLIFIED CONTIGUITY-PRESERVED LIBRARY FRAGMENTS OF GENOMIC DNA

CROSS-REFERENCE TO RELATED APPLICATION

This application claims the benefit of U.S. Provisional Application Ser. No. 62/942,563, filed Dec. 2, 2019, the contents of which is incorporated by reference herein in its entirety.

BACKGROUND

There are a variety of methods and applications for which it is desirable to generate a library of fragmented and tagged deoxyribonucleic acid (DNA) molecules from double-stranded DNA (dsDNA) molecules. Often, the purpose is to generate smaller DNA molecules (e.g., DNA fragments) from larger dsDNA molecules for use as templates in DNA sequencing reactions. The templates may enable short read lengths to be obtained. The short sequence reads typically overlap with a number of other short sequence reads to provide redundant coverage over different parts of the overall longer sequence. During data analysis, the overlapping sequences from numerous reads can be used to piece together the longer sequence information. As such, overlapping short sequence reads can be aligned to reconstruct the longer nucleic acid sequences. In some instances, pre-sequencing steps (such as barcoding of particular nucleic acid molecules) can be used to simplify the data analysis.

INTRODUCTION

A first aspect disclosed herein is a method comprising generating a series of time-based clustering images for a plurality of contiguity preserved library fragments from a genome sample, wherein each time-based clustering image in the series is sequentially generated by: introducing, to a flow cell, a respective sample including some of the contiguity preserved library fragments, wherein the some of the contiguity preserved library fragments are attached to a solid support or are attached to each other, initiating release of the some of the contiguity preserved library fragments from the solid support or from each other; amplifying the some of the contiguity preserved library fragments to generate a plurality of respective template strands; staining the respective template strands; and imaging the respective template strands.

A second aspect disclosed herein is a method comprising preparing a mixture including a plurality of contiguity preserved library fragments of a genome sample, the plurality of contiguity preserved library fragments being attached to solid supports or being attached to each other; diluting the mixture to generate a predetermined number of dilution samples to be introduced to a flow cell; and generating a time-based clustering image for at least one of the contiguity preserved library fragments by: introducing a first of the dilution samples including some of the contiguity preserved library fragments to the flow cell; initiating release of the some of the contiguity preserved library fragments from the solid support or from each other; amplifying the some of the contiguity preserved library fragments to generate a plurality of template strands; staining the plurality of template strands; and imaging the plurality of template strands.

A third aspect disclosed herein is a system comprising a flow cell receptacle; a fluidic control system including delivery fluidics to respectively deliver a dilution sample and a stain to a flow cell positioned in the flow cell receptacle; an illumination system positioned to illuminate the flow cell positioned in the flow cell receptacle; a detection system positioned to capture an image of the flow cell positioned in the flow cell receptacle; and a controller in operative communication with the fluidic control system, illumination system, and the detection system, the controller to: cause the delivery fluidics to introduce the dilution sample to the flow cell positioned in the flow cell receptacle; cause the delivery fluidics to introduce the stain to the flow cell positioned in the flow cell receptacle after template strands are generated in the flow cell positioned in the flow cell receptacle from contiguity preserved library fragments present in the dilution sample; cause the illumination system to illuminate the stained template strands in the flow cell positioned in the flow cell receptacle; and cause the detection system to image the illuminated, stained template strands in the flow cell positioned in the flow cell receptacle.

It is to be understood that any features of the first method and/or the second method and/or system disclosed herein may be combined together in any desirable manner and/or configuration and/or with any of the examples disclosed herein to achieve the benefits as described in this disclosure, including, for example, the identification of a particular group of template strands using a resolved cluster image.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 6A through FIG. 6D are schematic views of several steps in a method for generating series of time-based clustering images;

DETAILED DESCRIPTION

Figure 1:
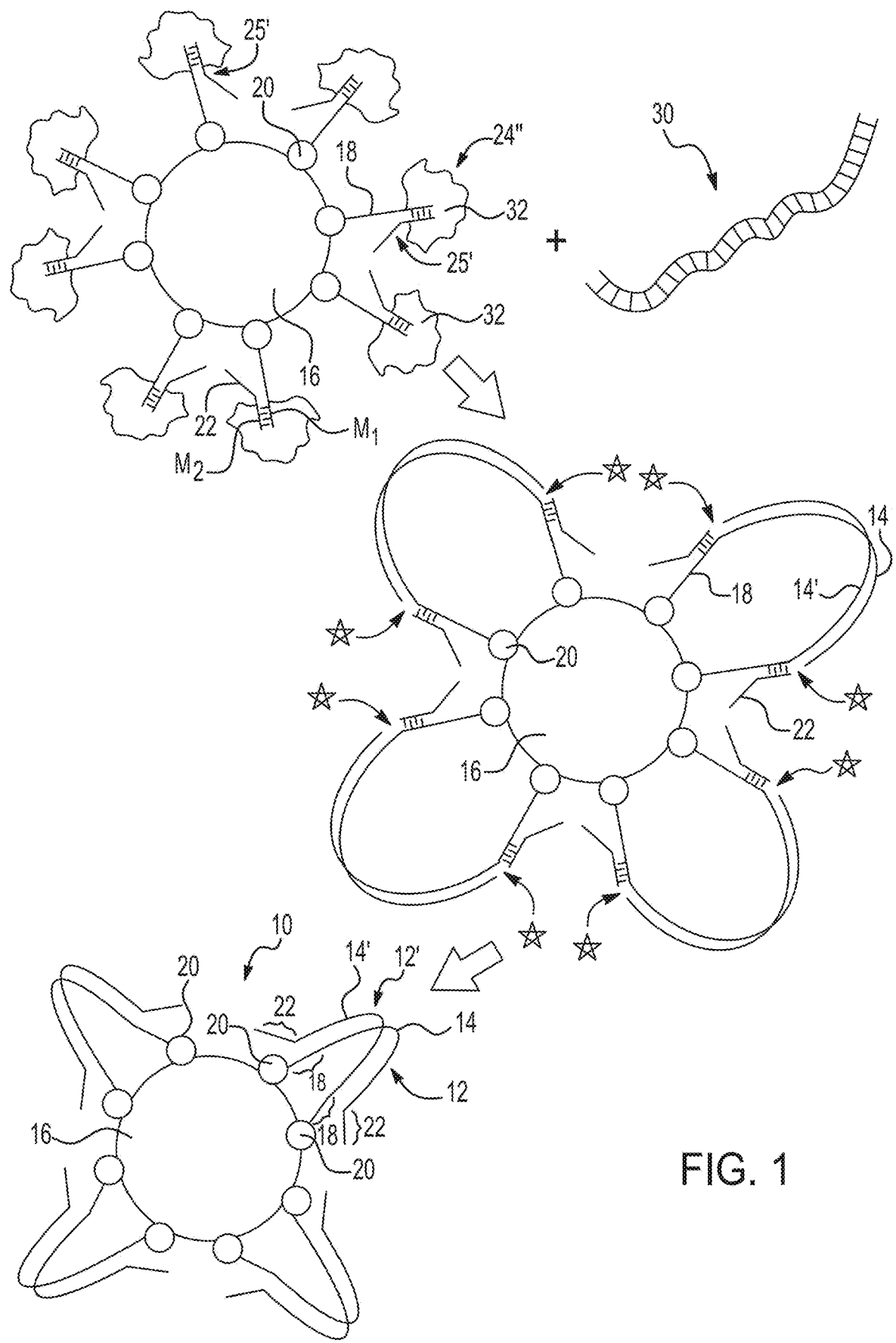
FIG. 1 is a schematic illustration of an example of a method for making an example of a complex including contiguity preserved library fragments attached to a solid support.

Library fragments are similarly sized (e.g., <1000 bp) deoxyribonucleic acid (DNA) pieces of a larger or longer DNA fragment. Library fragments can be grouped together in sequencing data if a common originating compartment can be identified in which the long DNA fragment originated. Compartmentalization of different long DNA fragments may be desirable in order to achieve sub-haploid genome content within each compartment for synthetic long reads. Synthetic long reads (or linked short reads) are enabled when a plurality of short fragments can be grouped together based on the identification of the compartment in which the long DNA fragment originated. Compartmentalization has been accomplished physically, for example, using wells, beads, droplets, or other physical compartments.

Common to all of these compartmentalization approaches is the principle that a barcode sequence or index sequence is used to identify the compartment in which the long DNA fragment originated. The barcode sequence attached to each of the shorter fragments may be unique to a particular long DNA fragment, and thus can help to mark different compartments during library preparation. It is the barcode sequence which is used to group short reads together to form synthetic long reads based on the assumption that the short reads all originate from the same compartment.

The example methods disclosed herein achieve compartmentalization of different library fragments without having to incorporate a unique barcode sequence. The method utilizes contiguity preserved library fragments (also referred to herein as "contiguity-preserved library fragments) and imaging to create a series of time-based clustering images. Each time-based clustering image can be used to identify a sample (compartment) from which a particular set of template strands was generated. Moreover, each sequenced read can be grouped using the time-based clustering images. This grouping allows the reads to the linked, thus enabling the reconstitution of a long DNA fragment.

Definitions

Terms used herein will be understood to take on their ordinary meaning in the relevant art unless specified otherwise. Several terms used herein and their meanings are set forth below.

As used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, unrecited elements or method steps.

Reference throughout the specification to "one example," "another example," "an example," and so forth, means that a particular element (e.g., feature, structure, composition, configuration, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, these terms can refer to less than or equal to ±5% from a stated value, such as less than or equal to ±2% from a stated value, such as less than or equal to ±1% from a stated value, such as less than or equal to ±0.5% from a stated value, such as less than or equal to ±0.2% from a stated value, such as less than or equal to ±0.1% from a stated value, such as less than or equal to ±0.05% from a stated value.

Adapter: A linear oligonucleotide sequence that can be fused to a nucleic acid molecule, for example, by ligation or tagmentation. Suitable adapter lengths may range from about 10 nucleotides to about 100 nucleotides, or from about 12 nucleotides to about 60 nucleotides, or from about 15 nucleotides to about 50 nucleotides. The adapter may include any combination of nucleotides and/or nucleic acids. In some examples, the adapter can include a sequence that is complementary to at least a portion of a primer, for example, a primer including a universal nucleotide sequence (such as a P5 or P7 sequence). As an example, the adapter at one end of a fragment includes a sequence that is complementary to at least a portion of a first flow cell primer, and the adapter at the other end of the fragment includes a sequence that is identical to at least a portion of a second flow cell primer. The complementary adapter can hybridize to the first flow cell primer, and the identical adapter is a template for its complementary copy, which can hybridize to the second flow cell primer during clustering. In some examples, the adapter can include a sequencing primer sequence or sequencing binding site. Combinations of different adapters may be incorporated into a nucleic acid molecule, such as a DNA fragment.

Capture site: A portion of a flow cell surface having been physically modified and/or modified with a chemical property that allows for localization of complexes. In an example, the capture site may include a chemical capture agent (i.e., a material, molecule or moiety that is capable of attaching, retaining, or binding to a target molecule (e.g., a complex)). One example chemical capture agent includes a member of a receptor-ligand binding pair (e.g., avidin, streptavidin, biotin, lectin, carbohydrate, nucleic acid binding protein, epitope, antibody, etc.) that is capable of binding to the target molecule (or to a linking moiety attached to the target molecule). Yet another example of the chemical capture agent is a chemical reagent capable of forming an electrostatic interaction, a hydrogen bond, or a covalent bond (e.g., thiol-disulfide exchange, click chemistry, Diels-Alder, etc.) with the complex.

Complex: A carrier, such as a solid support, and sequencing-ready nucleic acid fragments attached to the carrier. The carrier may also include one member of a binding pair whose other member is part of the capture site.

Fragment: A portion or piece of genetic material (e.g., DNA, RNA, etc.). Contiguity preserved library fragments are smaller pieces of the longer nucleic acid sample that has been fragmented, where the smaller fragments are held together in some manner (e.g., by a bead, with a transposome, etc.).

Nucleic acid molecule or sample: A polymeric form of nucleotides of any length, and may include ribonucleotides, deoxyribonucleotides, analogs thereof, or mixtures thereof. The term may refer to single stranded or double stranded polynucleotides.

A "template" nucleic acid molecule (or strand) may refer to a sequence that is to be analyzed.

The nucleotides in a nucleic acid sample may include naturally occurring nucleic acids and functional analogs thereof. Examples of functional analogs are capable of hybridizing to a nucleic acid in a sequence specific fashion or capable of being used as a template for replication of a particular nucleotide sequence. Naturally occurring nucleotides generally have a backbone containing phosphodiester bonds. An analog structure can have an alternate backbone linkage including any of a variety known in the art. Naturally occurring nucleotides generally have a deoxyribose sugar (e.g., found in DNA) or a ribose sugar (e.g., found in RNA). An analog structure can have an alternate sugar moiety including any of a variety known in the art. Nucleotides can include native or non-native bases. A native DNA can include one or more of adenine, thymine, cytosine and/or guanine, and a native RNA can include one or more of adenine, uracil, cytosine and/or guanine. Any non-native base may be used, such as a locked nucleic acid (LNA) and a bridged nucleic acid (BNA).

Primer A nucleic acid molecule that can hybridize to a target sequence, such as an adapter attached to a contiguity preserved library fragment. As one example, an amplification primer can serve as a starting point for template amplification and cluster generation. As another example, a synthesized nucleic acid (template) strand may include a site to which a primer (e.g., a sequencing primer) can hybridize in order to prime synthesis of a new strand that is complementary to the synthesized nucleic acid (template) strand. Any primer can include any combination of nucleotides or analogs thereof. In some examples, the primer is a single-stranded oligonucleotide or polynucleotide. The primer length can be any number of bases long and can include a variety of natural and/or non-natural nucleotides. In an example, the sequencing primer is a short strand, ranging from 10 to 60 bases, or from 20 to 40 bases.

Sequencing-ready nucleic acid fragments: A portion (e.g., contiguity preserved library fragment) of genetic material having adapters at the 3' and 5' ends. In the sequencing-ready nucleic acid fragment, each adapter includes a known universal sequence (e.g., which is complementary to at least a portion of a primer on a flow cell) and a sequencing primer sequence. A sequencing-ready nucleic acid fragment may be bound via insertion of transposons bound to the surface of a solid support (e.g., bead), or directly immobilized through a binding pair or other cleavable linker.

Solid support: A small body made of a rigid or semi-rigid material having a shape characterized, for example, as a sphere, oval, microsphere, or other recognized particle shape whether having regular or irregular dimensions. The solid support can have a sequencing library attached thereto. Example materials that are useful for the solid support include, without limitation, glass; plastic, such as acrylic, polystyrene or a copolymer of styrene and another material, polypropylene, polyethylene, polybutylene, polyurethane or polytetrafluoroethylene (TEFLON® from The Chemours Co); polysaccharides or cross-linked polysaccharides such as agarose or Sepharose; nylon; nitrocellulose; resin; silica or silica-based materials including silicon and modified silicon; carbon-fiber, metal; inorganic glass; optical fiber bundle, or a variety of other polymers. Example solid supports include controlled pore glass beads, paramagnetic beads, thoria sol, SEPHAROSE® beads (cross-linked beaded form of agarose, available from Cytivia), nanocrystals and others known in the art as described, for example, in *Microsphere Detection Guide* from Bangs Laboratories, Fishers Ind.

Transposome: A complex formed between an integration enzyme (e.g., an integrase or a transposase) and a transferrable strand, a non-transferrable strand, or both transferrable and non-transferrable strands.

Contiguity Preserved Library Fragments

In the examples disclosed herein, the library fragments that are introduced to the flow cell are contiguity preserved library fragments. Contiguity preserved library fragments are smaller pieces of a longer nucleic acid sample that has been fragmented, where the smaller pieces are physically held together in some manner. In some examples disclosed herein, the contiguity may be preserved using a solid support in library preparation. In other examples disclosed herein, the contiguity may be preserved by creating fragments that are attached to one another during initial library preparation through bound transposomes, introducing the attached fragments to the flow cell, and then completing the library preparation on the flow cell.

FIG. 1 depicts an example of a method for forming a complex 10 including sequencing-ready nucleic acid fragments 12 including fragments 14 from the larger nucleic acid sample, whose contiguity is preserved on a solid support 16.

In one example method to form the complex 10 shown in FIG. 1, an adapter sequence 18 is bound to the solid support 16 through one member 20 of a binding pair. In an example, this adapter sequence 18 may include a first sequencing primer sequence (e.g., a read 1 sequencing primer sequence) and a first sequence (P5') that is complementary to at least a portion of one of the amplification primers (e.g., P5) on the flow cell (shown in FIGS. 5A and 5B). The adapter sequence 18 is bound to the one member 20 of the binding pair (e.g., biotin) so that it can be bound to the surface of the solid support 16, which includes the other member (e.g., avidin, streptavidin, etc.) of the binding pair.

As shown in FIG. 1 a transposome complex 24" may also be bound to the solid support 16. Prior to loading the transposome complex 24" on the solid support 16, a partial Y-adapter 25' may be mixed with a transposase enzyme 32 (which, while not shown, may include two Tn5 molecules) to form an example of the transposome complex 24". The partial Y-adapter 25' may include two mosaic end sequences $M_1$, $M_2$ that are hybridized to each other. One of the mosaic end sequences $M_1$ has a free end that is able to attach to the fragmented DNA strands during tagmentation, and thus is similar to the transferred strand 26 in FIG. 2A through FIG. 2C. The other of the mosaic end sequences $M_2$ may be attached to a second sequencing primer sequence (e.g., a read 2 sequencing primer sequence), and a second sequence (P7) that has the same sequence as at least a portion of another of the amplification primers (P7) on the flow cell, so that its copy is complementary (e.g., P7') to the amplification primer (P7). In this example, the other of the mosaic end sequences $M_2$, the second sequencing primer sequence and the second sequence make up adapter sequence 22. The adapter sequences 22 are not attached to the fragmented DNA strands during tagmentation, and thus are similar to the non-transferred strands 28 in FIG. 2A through FIG. 2C.

Loading the transposome complex 24" on the solid support 16 may involve mixing the transposome complex 24" with the solid support 16, and exposing the mixture to suitable conditions for ligating the mosaic end $M_1$ of the partial Y-adapter 25' to the 3'-end of the adapter sequence 18. As shown in FIG. 1, individual transposome complexes 24" may be attached to each of the adapter sequences 18 on the solid support 16.

In this example method to form the complex 10, a tagmentation process may then be performed. A fluid (e.g., a tagmentation buffer) including the longer nucleic acid sample 30 (e.g., DNA) may be added to the solid support 16 having the adapter sequence 18 and the transposome complexes 24" bound thereto. As the sample contacts the transposome complexes 24", the longer nucleic acid sample is tagmented. During this example of tagmentation, the sample 30 is fragmented into fragments 14, 14', and each of the fragments 14, 14' is tagged, at its 5' end, with the free end of the mosaic end $M_1$ of the partial Y-adapter 25'.

As shown in FIG. 1, tagmentation of the longer nucleic acid sample 30 results in a plurality of bridged molecules between the transposome complexes 24". The bridged molecules wrap around the solid support 16. The transposome complexes 24" and the adapter sequences 18 maintain the contiguity of the nucleic acid sample 30 as bridged molecules, and thus the bridged molecules are the contiguity preserved library fragments 14, 14'.

The transposase enzyme may then be removed via sodium dodecyl sulfate (SDS) treatment or heat or proteinase K digestion. Removal of the transposase enzymes leaves the contiguity preserved library fragments 14, 14' attached to the solid support 16.

To complete the sequencing ready fragments, further extension and ligation (denoted by the stars in FIG. 1) is undertaken to ensure fragments 14 and 14' are attached to sequences 22. The resulting complex 10 is shown in FIG. 1.

Each contiguity preserved library fragment 14, 14' is part of a respective sequencing-ready nucleic acid fragments 12, 12', each of which also includes respective adapter sequences 18 and 22 attached at either end. The adapter sequences 18 are those initially bound to the solid support 16, and include the first sequencing primer sequence and the first sequence complementary to one of the flow cell primers. The adapter sequences 18 are attached to the one member 20 of a binding pair. The adapter sequences 22 are from the partial Y-adapter 25', and include the second sequence identical to another flow cell primer and the second sequencing primer sequence. Because each sequencing-ready nucleic acid fragment 14, 14' includes suitable adapters for bridge amplification and sequencing, PCR amplification is not performed. These fragments 12, 12' are thus sequencing-ready. Moreover, because the contiguity preserved library fragments 14, 14' are from the same longer nucleic acid sample 30, the contiguity preserved library fragments 14, 14' may be suitable for the linked long read applications disclosed herein.

Figure 2A:
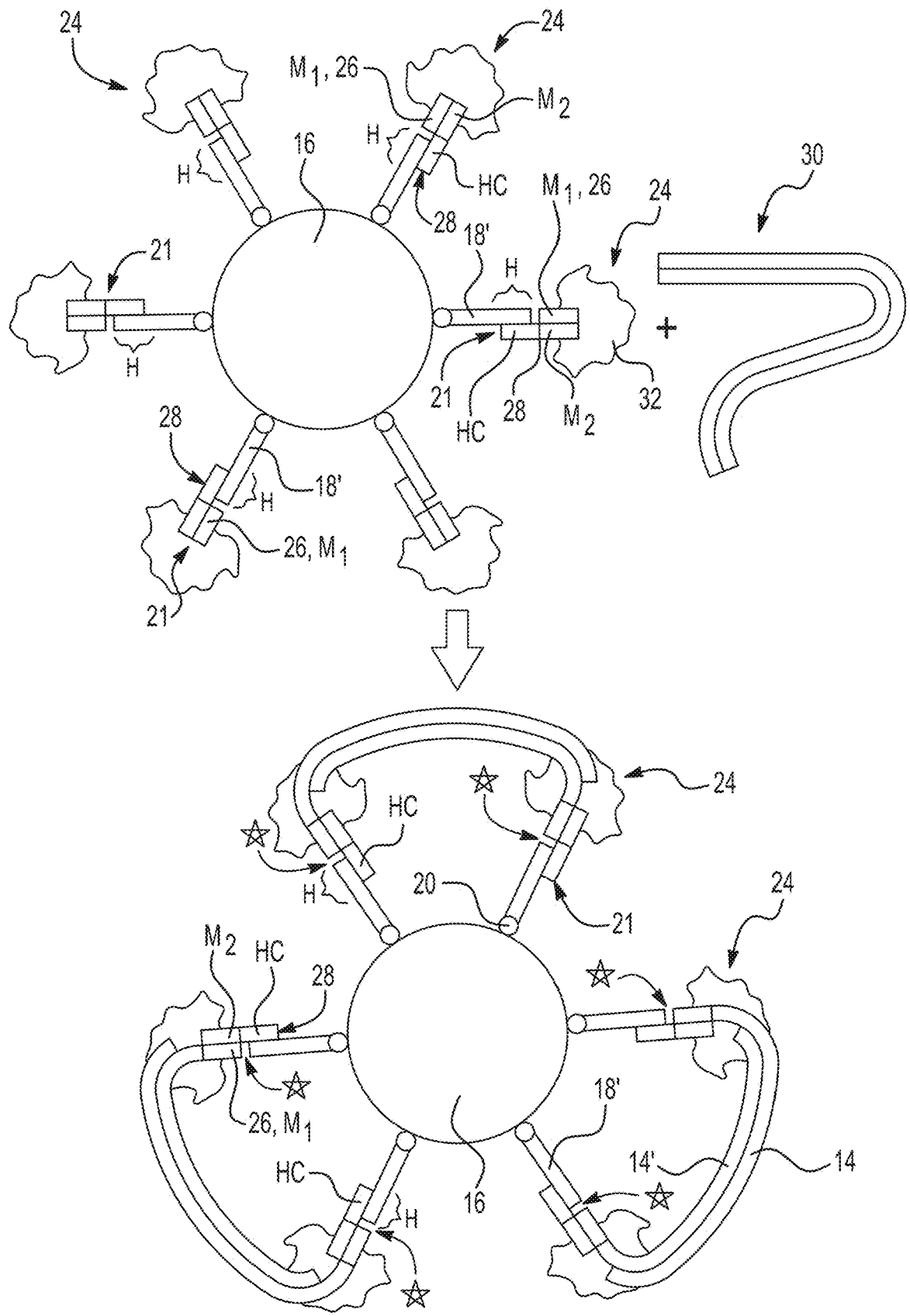
FIG. 2A through FIG. 2C are schematic illustrations which together illustrate another example of a method for making another example of a complex including contiguity preserved library fragments attached to a solid support.
Figure 2B:
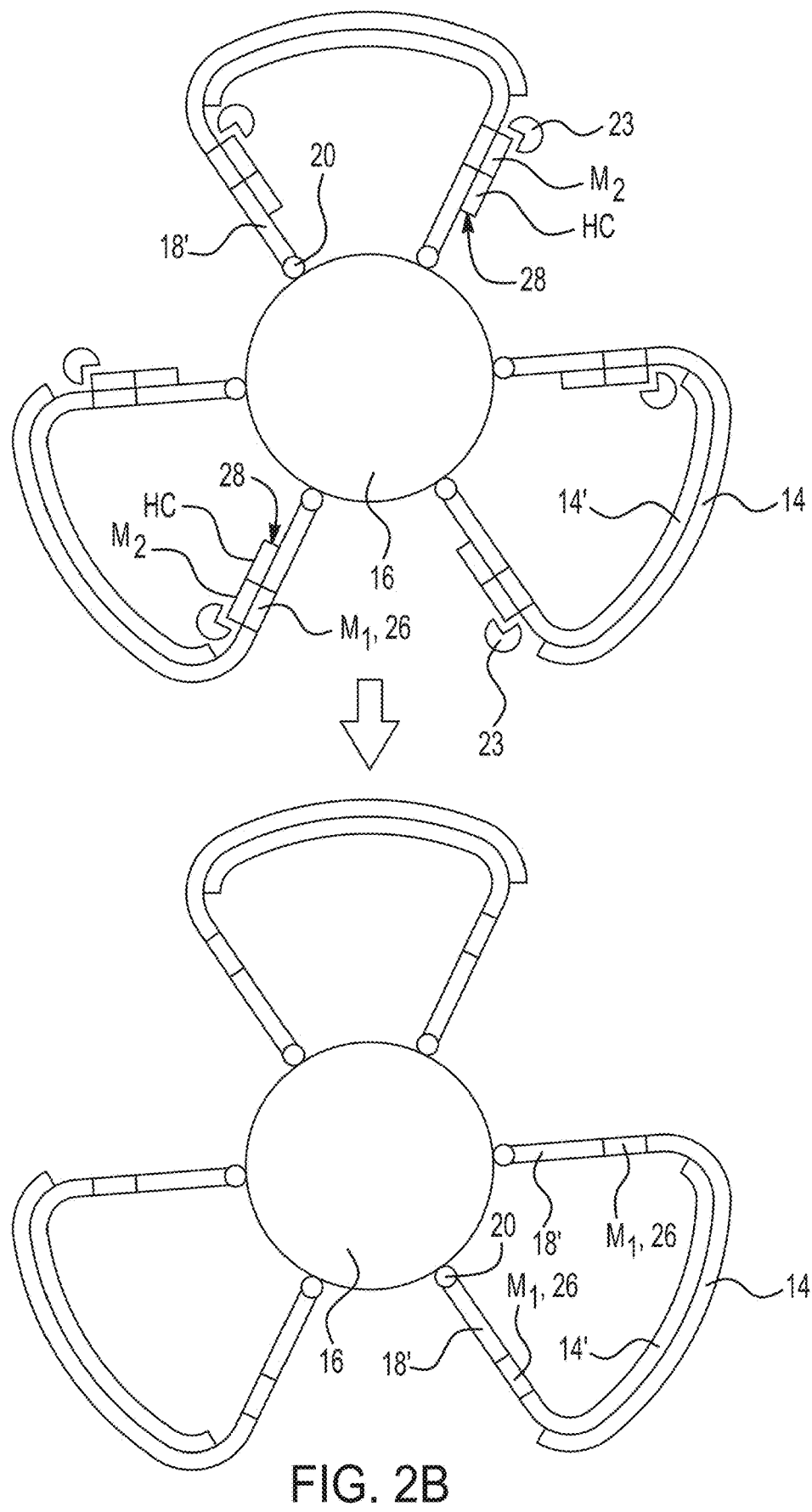
Figure 2C:
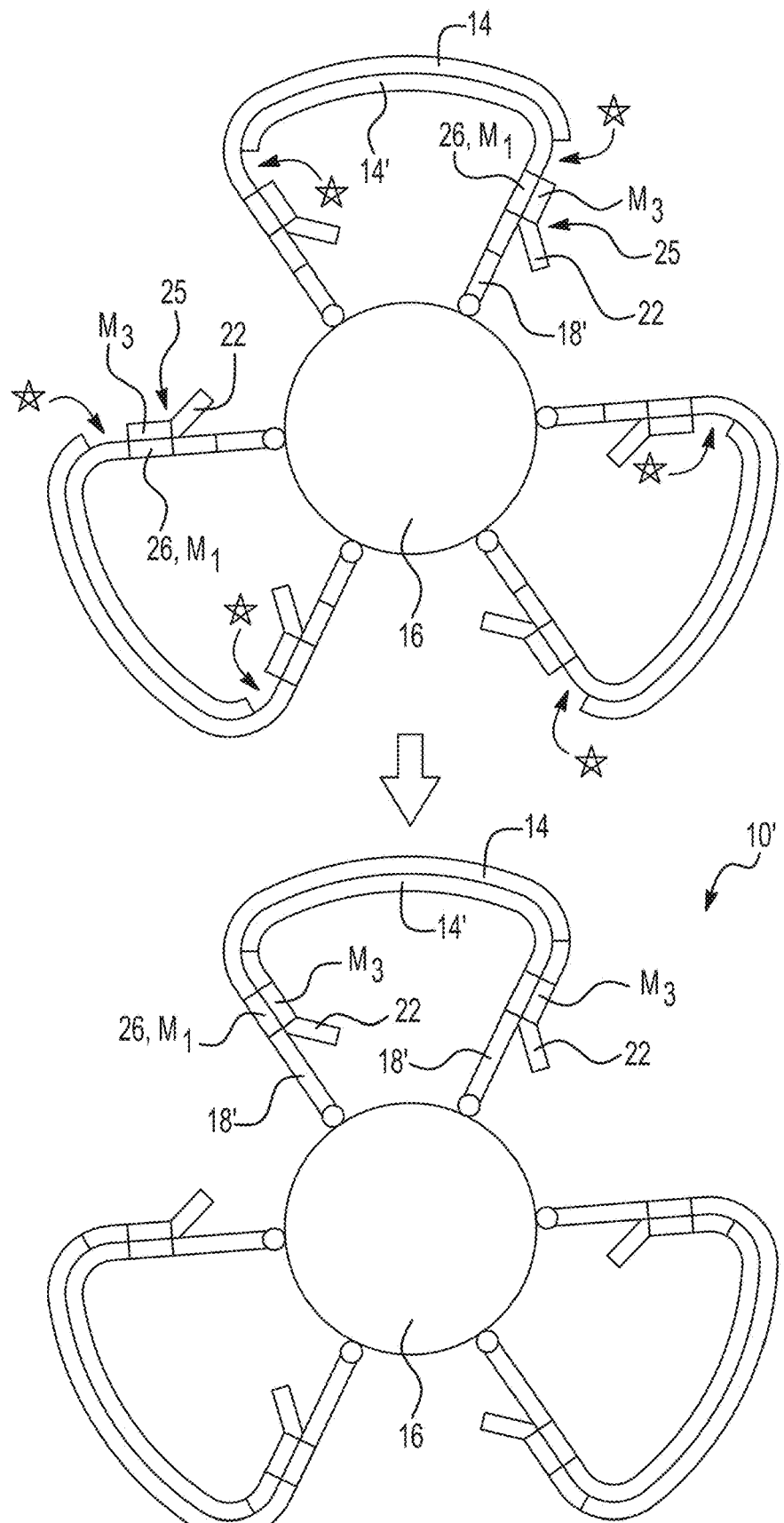

Another example method for forming another example complex 10' (FIG. 2C) is depicted in FIG. 2A through FIG. 2C.

In this example method, the adapter sequence 18' is bound to the solid support 16 through one member 20 of a binding pair. In an example, this adapter sequence 18' may include a hybridizable sequence H, a first sequencing primer sequence (e.g., a read 1 sequencing primer sequence) and a first sequence (e.g., P5) that is identical to at least a portion of one of the amplification primers (e.g., P5) on the flow cell, so that its copy is complementary (e.g., P5') to the amplification primer (P5). The adapter sequence 18' is bound to the one member 20 of the binding pair (e.g., biotin) so that it can be bound to the surface of the solid support 16, which includes the other member (e.g., avidin, streptavidin, etc.) of the binding pair.

As shown in FIG. 2A, a transposome complex 24 may also be bound to the solid support 16. Prior to loading the transposome complex 24 on the solid support 16, an L-adapter 21 may be mixed with a transposase enzyme 32 (e.g., including two Tn5 molecules) to form an example of the transposome complex 24. The L-adapter 21 may include two mosaic end sequences $M_1$, $M_2$ that are hybridized to each other. One of the mosaic end sequences $M_1$ is a transferred strand 26 that is added to one end of each fragment 14, 14' during a ligation process that takes place after a tagmentation process. The other of the mosaic end sequences $M_2$ is part of a non-transferred strand 28 that is removed after the ligation and tagmentation processes. This mosaic end sequence $M_2$ is attached to a complementary hybridizable sequence HC which is complementary to the hybridizable sequence H of the adapter sequence 18' attached to the solid support 16. The complementary hybridizable sequence HC enables the L-adapter 21 to hybridize to the adapter sequence 18'. Thus, the complementary hybridizable sequence HC enables the transposome complex 24 to be loaded onto the solid support.

Loading the transposome complex 24 on the solid support 16 may involve mixing the transposome complex 24 with the solid support 16, and exposing the mixture to suitable conditions for the hybridization of the complementary hybridizable sequence HC of the L-adapter 21 to the hybridizable sequence H of the adapter sequence 18'. As shown in FIG. 2A, individual transposome complex 24 may be attached to each of the adapter sequences 18' on the solid support 16.

In this example method to form the complex 10', a tagmentation process is then performed. A fluid (e.g., a tagmentation buffer) including the longer nucleic acid sample (e.g., DNA) 30 may be added to the solid support 16 having the transposome complex 24 loaded thereon. As the sample 30 contacts the solid support-bound transposome complexes 24, the longer nucleic acid sample 30 is tagmented. During this example of tagmentation, the sample 30 is fragmented into fragments 14, 14', and each of the fragments 14, 14' is tagged, at its 5'-end, with the mosaic end sequence $M_1$ of the L-adapter 21.

As shown in FIG. 2A, tagmentation of the longer nucleic acid sample 30 results in a plurality of bridged molecules between adjacent transposome complexes 24, and thus adjacent adapter sequences 18'. The bridged molecules wrap around the solid support 16. The transposome complexes 24 and adapter sequences 18' maintain the contiguity of the nucleic acid sample 30 as bridged molecules, and thus the bridged molecules are the contiguity preserved library fragments 14, 14'.

The transposase enzyme 32 may then be removed via sodium dodecyl sulfate (SDS) treatment or heat or proteinase K digestion.

Ligation may then be performed to bind the free mosaic end sequences $M_1$ to the respective adapter sequences 18'. In FIG. 2A, the stars represent where ligation is performed. In an example, ligation may be initiated by introducing a buffer containing a suitable ligase, and heating to about suitable temperature for a suitable time to initiate enzyme activity. Examples of suitable ligase enzymes include *E. Coli* DNA ligase, T7 ligase, etc. In an example, the buffer containing *E. Coli* DNA ligase may also include nicotinamide adenine dinucleotide (NAD$^+$). In this example, heating to about 16°

C. for about 15 minutes initiates the enzyme activity. The resulting structure is shown in FIG. 2B.

The non-transferred strand 28 of the L-adapter 21 may then be removed. In this example, each of the non-transferred strands 28 is removed using any suitable 5'-3' exonuclease enzyme 23, such as T7 exonuclease. In an example, non-transferred strand removal may be initiated by introducing a buffer containing the 5'-3' exonuclease enzyme 23, and waiting for a predetermined time. The 5'-3' exonuclease enzyme 23 is able to digest the non-transferred strand 28 at room temperature (e.g., from about 22° C. to about 25° C.), and thus additional heating is not used. The digested non-transferred strands 28 can then be washed away.

Figure 11:
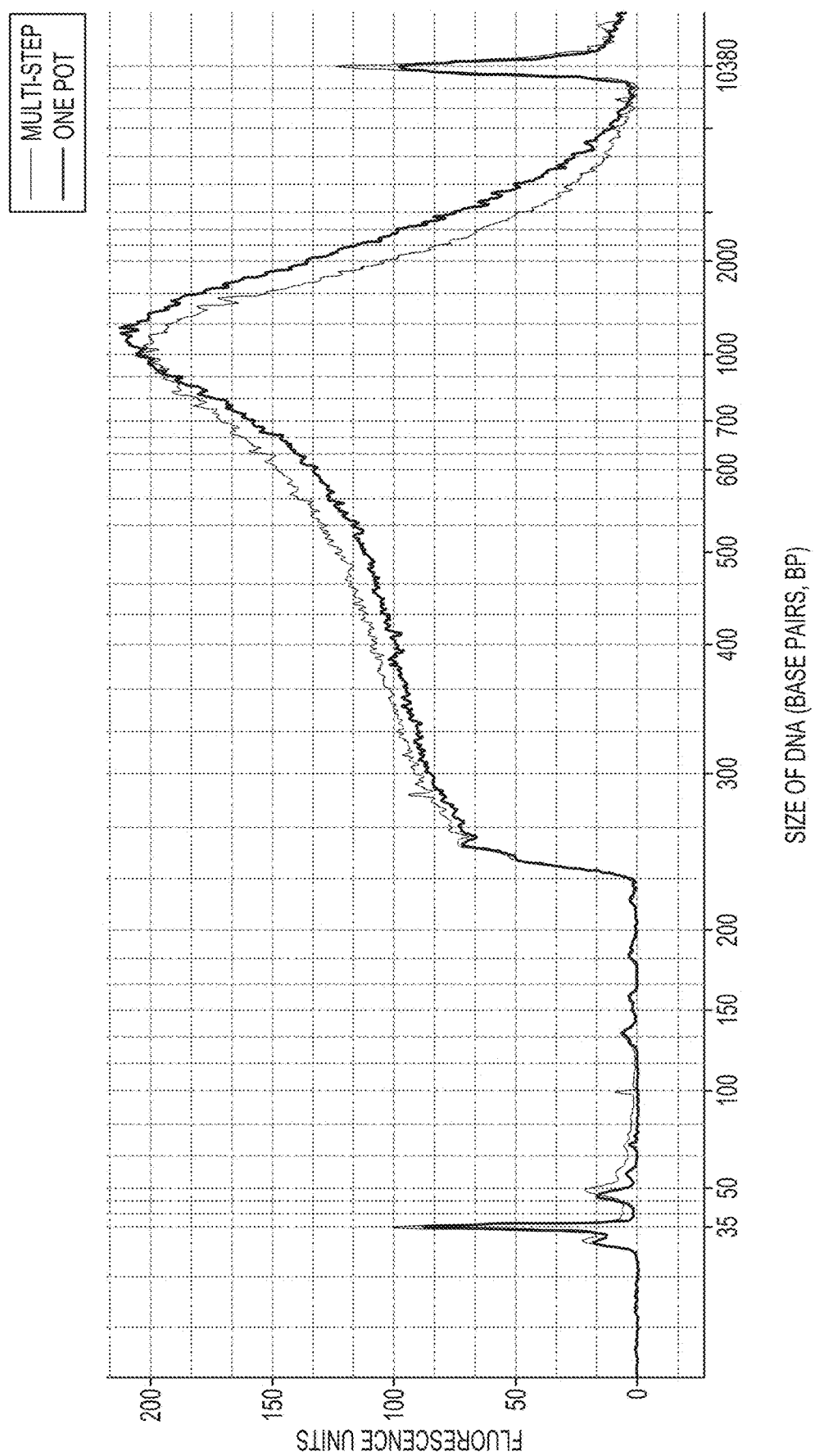
FIG. 11 is a graph depicting the fluorescence (Y-axis, fluorescence units) versus of the size (X-axis, base pairs) of PCR-amplified library fragments generated by the methods shown in FIG. 2A through FIG. 2C and in FIG. 3.

Using an exonuclease enzyme to remove the non-transferred strands 28 may be more desirable than using heat denaturation. The 5'-3' exonuclease enzyme 23 efficiently digests the non-transferred strands 28, yielding a cleaner template (than when heat denaturation is used) for hybridization of a subsequently attached adapter sequence (see reference numerals 22 in FIG. 2C). This can improve the library yield. Additionally, removing the non-transferred strands 28 via 5'-3' exonuclease enzyme 23 can improve library coverage over adenine (A) and thymine (T) rich regions, losses of which have been observed after heat denaturation of the non-transferred strands 28 (see FIG. 11). Still further, digestion via the exonuclease enzyme does not increase the time of the overall library preparation process.

Referring now to FIG. 2C, this example of the method to form the complex 10' involves introducing a partial Y-adapter 25. The partial Y-adapter 25 includes a mosaic end sequence $M_3$ that is complementary to the mosaic end sequence $M_1$ and an adapter sequence 22. The adapter sequence 22 may include a second sequencing primer sequence (e.g., a read 2 sequencing primer sequence), and a second sequence (P7') that is complementary to another of the amplification primers (P7) on the flow cell. As shown in FIG. 2C, the mosaic end sequence $M_3$ of the partial Y-adapter 25 hybridizes to the mosaic end sequence $M_1$ of the transferred strand 26 (now ligated to the adapter sequence 18'), and thus attaches the partial Y-adapter 25 to the solid support 16.

In the examples disclosed herein, the adapter sequences 18, 18' and/or 22 may also include a sequencing sample index or a barcode sequence. These sequences may be used as a backup or alternative to the compartmentalization methods disclosed herein.

To generate sequencing ready fragments, further extension and ligation is undertaken to ensure fragments 14 and 14' are attached to the mosaic end sequence $M_3$, and thus the sequences 22.

The resulting complex 10' is shown in FIG. 2C.

Figure 3:
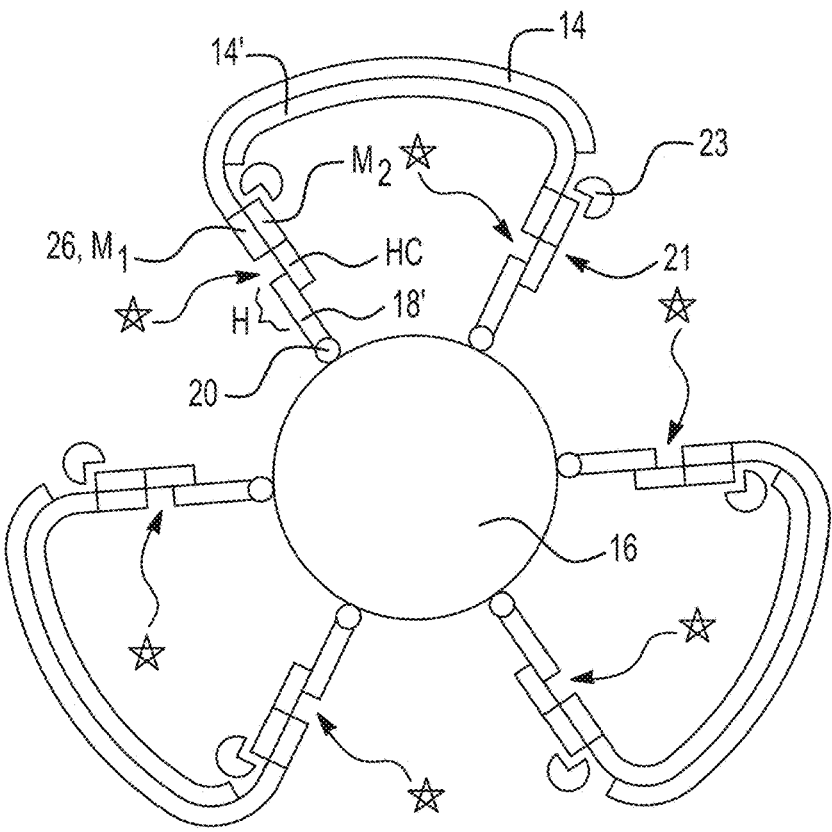
FIG. 3 is a schematic illustration of the ligation and digestion of the method of FIG. 2A through FIG. 2C taking place in a single, one pot reaction.

Yet another example method for forming the complex 10' (shown in FIG. 2C) is partially depicted in FIG. 3. In this example method, ligation of the transferred strand 26 and digestion of the non-transferred strand 28 are performed as part of a single, one-pot protocol.

In this example method, the adapter sequence 18' is bound to the solid support 16 through one member 20 of a binding pair. The adapter sequence 18' as described in reference to FIG. 2A may be used, which includes the hybridizable sequence H, the first sequencing primer sequence (e.g., a read 1 sequencing primer sequence), and the first sequence (P5) that is identical to at least a portion of one of the amplification primers (e.g., P5) on the flow cell, so that its copy is complementary (e.g., P5') to the amplification primer (P5). Also in this example method, the transposome complex 24 is loaded on the solid support 16 as described in reference to FIG. 2A. Briefly, the complementary hybridizable sequence HC of the L-adapter 21 of the transposome complex 24 is hybridized to the hybridizable sequence H of the adapter sequence 18'.

In this example method to form the complex 10' (FIG. 2C), tagmentation is performed as described in reference to FIG. 2A.

Ligation of the transferred strand 26 and digestion of the non-transferred strand 28 may then be performed together. This is schematically illustrated in FIG. 3. For the ligase and the exonuclease enzyme to work synergistically, the reagent formulation that is introduced to the tagmented solid support includes a buffer, the ligase enzyme, the 5'-3' exonuclease enzyme 23 (e.g., T7 exonuclease), and any other component required by the respective enzymes (e.g., a cofactor, such as $NAD^+$). In an example, ligation and digestion may be initiated by introducing the reagent formulation, and heating to about 25° C. for about 15 minutes to initiate enzyme activity.

Incorporating the ligase and the exonuclease enzyme into the same reagent formulation can decrease protocol time (e.g., by about 10 minutes compared to the example method shown in FIG. 2A through FIG. 2C), and also reduces the number of wash steps.

This example of the method then continues with introducing the partial Y-adapter 25, as described in reference to FIG. 2C. To generate sequencing ready fragments and the final complex 10', further extension and ligation is undertaken to ensure fragments 14 and 14' are attached to the mosaic end sequence $M_3$, and thus the sequences 22.

The methods described in reference to FIG. 1, FIG. 2A-FIG. 2C, and FIG. 3 for making the complexes 10, 10' provide a few examples, but it is to be understood that other methods may be used as long as sequencing-ready nucleic acid fragments 12, 12' are attached to the solid support 16.

In other examples disclosed herein, the contiguity information may be preserved by performing a portion of the library preparation off of the flow cell, and performing a portion of the library preparation on the flow cell.

Figure 4:
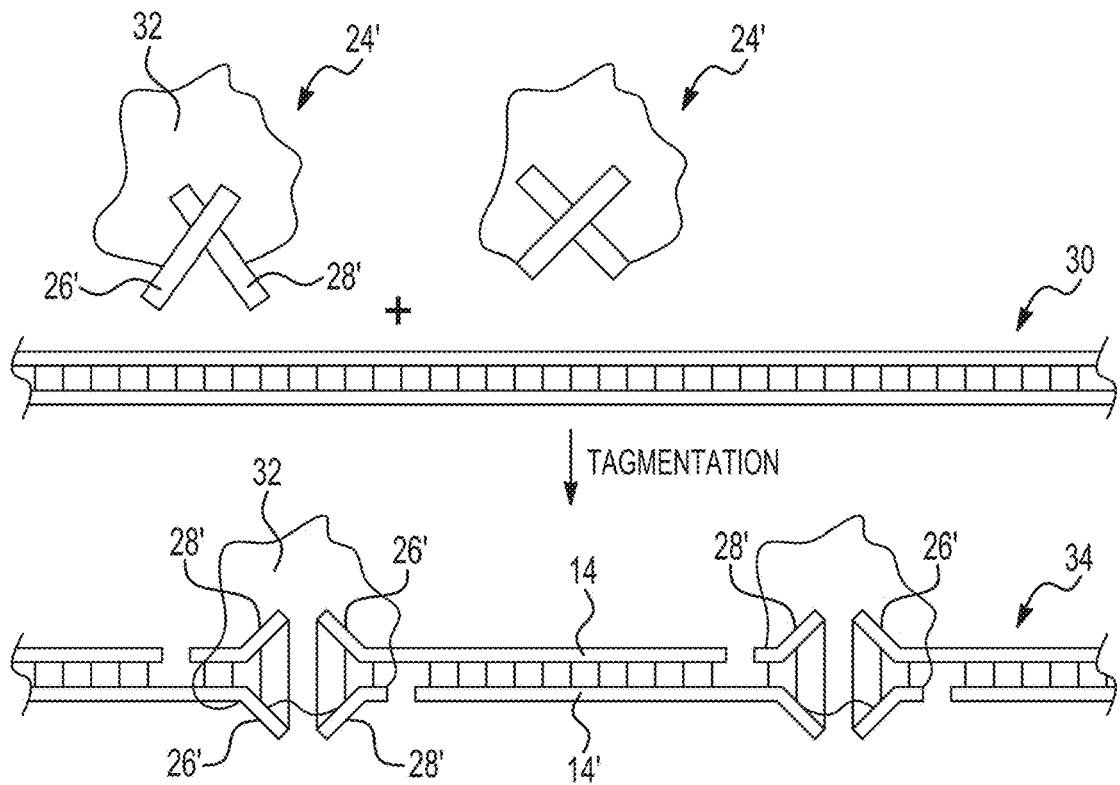
FIG. 4 is a schematic illustration of an example of a portion of a library preparation process that generates attached contiguity preserved library fragments.

In this example, library preparation may be initiated outside of the flow cell using tagmentation, as shown schematically in FIG. 4.

In the example shown, a fluid (e.g., a tagmentation buffer) including the longer nucleic acid sample 30 (e.g., double stranded DNA) may be mixed with transposome complexes 24'. In the example shown in FIG. 4, each transposome complex 24' is a dimer, including two transposase enzymes (which are collectively shown as "32" in FIG. 4), a transferred strand 26', and a non-transferred strand 28'. In other examples, different transposome complexes may be used, for example, one of which includes the transposase enzymes 32 and the transferred strand 26' and another of which includes the transposase enzymes 32 and the non-transferred strand 28'.

In this example, the transferred strands 26' are adapters that are added to one end of each fragment 14, 14' during the tagmentation process. In an example, each transferred strand 26 is an adapter including a first sequencing primer sequence (e.g., a read 1 sequencing primer sequence) and a first sequence (P5') that is complementary to at least a portion of one of the amplification primers (e.g., P5) on the flow cell.

In this example, the non-transferred strands 28' are adapters that are not incorporated into the fragment 14, 14' during tagmentation, but rather, may be subsequently ligated to the other end of each fragment 14, 14'. As shown in FIG. 4, the non-transferred strands 28' may be attached to the transferred strand 26' via at least partial base-pairing during tagmentation. In this example, the non-transferred strand 28' is an adapter including a second sequencing primer sequence (e.g., a read 2 sequencing primer sequence) and a second sequence (P7) that is identical to at least a portion of one of the amplification primers (e.g., P7) on the flow cell, so that its copy is complementary (e.g., P7') to the amplification primer (P7).

As shown in FIG. 4, within the fluid, the transposomes 24' fragment the longer nucleic acid sample 30 into fragments 14, 14' and ligate the transferred strands 26' to the 5' end of each fragment 14, 14'. In an example, the transferred strand 26' is incorporated to the 5'-end of each fragment 14, 14' of the longer nucleic acid sample 30 by one-sided transposition. The non-transferred strands 28' may be attached to the transferred strand 26' via base-pairing.

This example tagmentation process maintains the contiguity of the longer nucleic acid sample 30 because the generated fragments 14, 14' (and any transferred strands 26' and non-transferred strands 28' directly or indirectly attached thereto) remain attached to one another via the transposase 32. The attached contiguity preserved library fragments 14, 14' are referred to herein as the attached fragments 34.

As mentioned herein, the attached fragments 34 may be introduced to the flow cell, where additional processing may be performed to complete library preparation. This is shown schematically in FIG. 8, which will be described further in reference to the methods disclosed herein.

Flow Cell

Figure 5A:
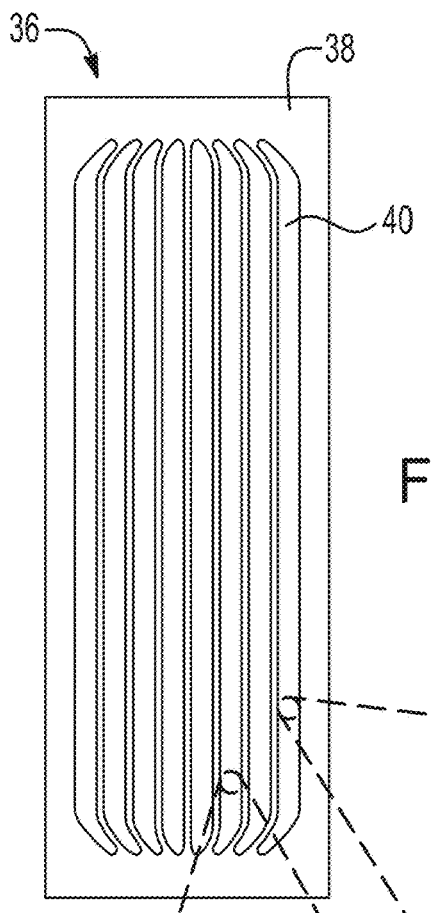
FIG. 5A is a top view of an example of a flow cell.

The methods disclosed herein may utilize a flow cell 36, an example of which is depicted in FIG. 5A. The flow cell 36 includes a substrate 38 that at least partially define a lane or flow channel 40.

The substrate 38 may be a single layer/material. Examples of suitable single layer substrates include epoxy siloxane, glass, modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon (polyamides), ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($Ta_2O_5$) or other tantalum oxide(s) ($TaO_x$), hafnium oxide ($HaO_2$), carbon, metals, inorganic glasses, or the like. The substrate 38 may also be a multi-layered structure. Some examples of the multi-layered structure include glass or silicon, with a coating layer of tantalum oxide or another ceramic oxide at the surface. Other examples of the multi-layered structure include an underlying support (e.g., glass or silicon) having a patterned resin thereon. Still other examples of the multi-layered substrate may include a silicon-on-insulator (SOI) substrate.

In an example, the substrate 38 may have a diameter ranging from about 2 mm to about 300 mm, or a rectangular sheet or panel having its largest dimension up to about 10 feet (~3 meters). In an example, the substrate 38 is a wafer having a diameter ranging from about 200 mm to about 300 mm. In another example, the substrate 38 is a die having a width ranging from about 0.1 mm to about 10 mm. While example dimensions have been provided, it is to be understood that a substrate 38 with any suitable dimensions may be used. For another example, a panel may be used that is a rectangular support, which has a greater surface area than a 300 mm round wafer.

In the example shown in FIG. 5A, the flow cell 36 includes flow channels 40. While several flow channels 40 are shown, it is to be understood that any number of channels 40 may be included in the flow cell 36 (e.g., a single channel 40, four channels 40 etc.). Each flow channel 40 is an area defined between two bonded components (e.g., the substrate 36 and a lid or two substrates 36), which can have fluids (e.g., those describe herein) introduced thereto and removed therefrom. Each flow channel 40 may be isolated from each other flow channel 40 so that fluid introduced into any particular flow channel 40 does not flow into any adjacent flow channel 40. Some examples of the fluids introduced into the flow channels 40 may introduce reaction components (e.g., contiguity preserved library fragments 14, 14' (e.g., on the solid support 16 or attached to one another), polymerases, sequencing primers, nucleotides, etc.), washing solutions, deblocking agents, etc.

The flow channel 40 may be defined in the substrate 38 using any suitable technique that depends, in part, upon the material(s) of the substrate 38. In one example, the flow channel 40 is etched into a glass substrate 38. In another example, the flow channel 40 may be patterned into a resin of a multi-layered substrate 38 using photolithography, nanoimprint lithography, etc. In still another example, a separate material (not shown) may be applied to the substrate 38 so that the separate material defines the walls of the flow channel 40 and the substrate 38 defines the bottom of the flow channel 40.

In an example, the flow channel 40 has a rectilinear configuration. The length and width of the flow channel 40 may be smaller, respectively, than the length and width of the substrate 38 so that portion of the substrate surface surrounding the flow channel 40 is available for attachment to a lid (not shown) or another substrate 38. In some instances, the width of each flow channel 40 can be at least about 1 mm, at least about 2.5 mm, at least about 5 mm, at least about 7 mm, at least about 10 mm, or more. In some instances, the length of each lane/flow channel 40 can be at least about 10 mm, at least about 25 mm, at least about 50 mm, at least about 100 mm, or more. The width and/or length of each flow channel 40 can be greater than, less than or between the values specified above. In another example, the flow channel 40 is square (e.g., 10 mm×10 mm).

The depth of each flow channel 40 can be as small as a monolayer thick when microcontact, aerosol, or inkjet printing is used to deposit a separate material that defines the flow channel walls. The depth may be larger when a separate material (not shown) is used to bond the lid to the substrate 38 or to bond two substrates 38 together. For other examples, the depth of each flow channel 40 can be about 1 μm, about 10 μm, about 50 μm, about 100 μm, or more. In an example, the depth may range from about 10 μm to about 100 μm. In another example, the depth may range from about 10 μm to about 30 μm. In still another example, the depth is about 5 μm or less. It is to be understood that the depth of each flow channel 40 be greater than, less than or between the values specified above.

Figure 5B:
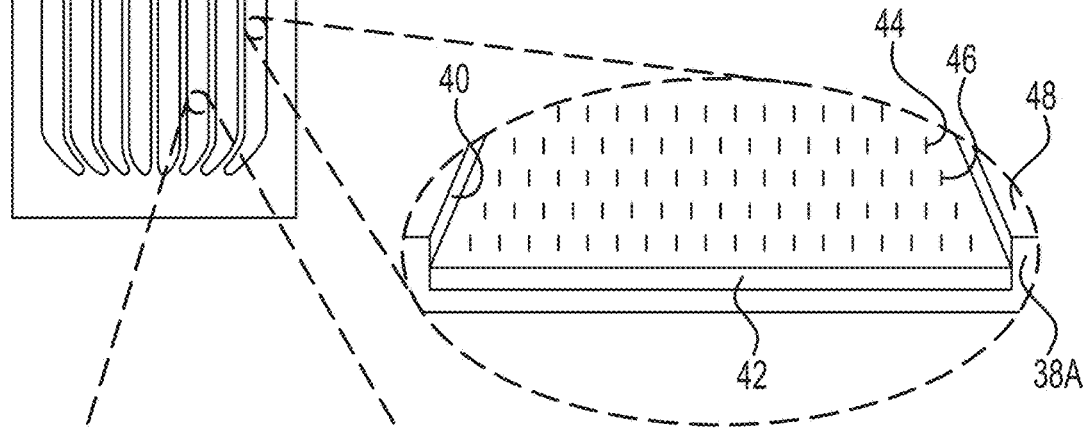
FIG. 5B is an enlarged, and partially cutaway view of an example of a flow channel of the flow cell.
Figure 5C:
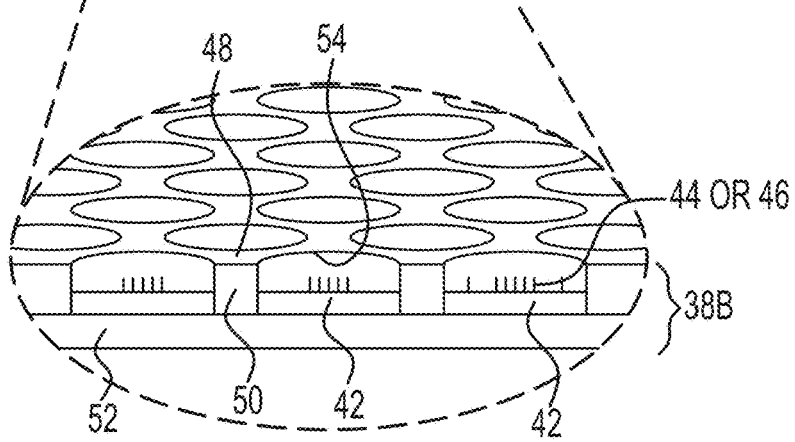
FIG. 5C is an enlarged, and partially cutaway view of another example of a flow channel of the flow cell.

Different examples of the architecture within the flow channels 40 of the flow cell 36 are shown FIG. 5B and FIG. 5C.

In the example shown in FIG. 5B, the flow cell 36 includes a single layer substrate 38A and the flow channel 40 defined at least partially in the single layer substrate 38A.

A polymeric hydrogel 42 is present in the flow channel 40. An example of the polymeric hydrogel 42 includes an acrylamide copolymer, such as poly(N-(5-azidoacetamidylpentyl)acrylamide-co-acrylamide, PAZAM. PAZAM and some other forms of the acrylamide copolymer are represented by the following structure (I):

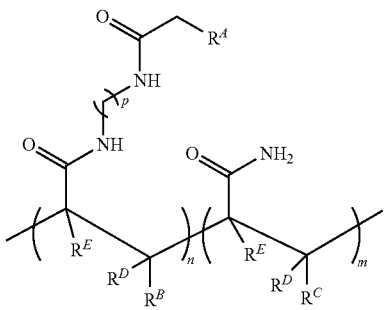

wherein:

$R^A$ is selected from the group consisting of azido, optionally substituted amino, optionally substituted alkenyl, optionally substituted alkyne, halogen, optionally substituted hydrazone, optionally substituted hydrazine, carboxyl, hydroxy, optionally substituted tetrazole, optionally substituted tetrazine, nitrile oxide, nitrone, sulfate, and thiol;

$R^B$ is H or optionally substituted alkyl;

$R^C$, $R^D$, and $R^E$ are each independently selected from the group consisting of H and optionally substituted alkyl;

each of the $-(CH_2)_p-$ can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in structure (I) are representative, and the monomeric subunits may be present in any order in the polymer structure (e.g., random, block, patterned, or a combination thereof).

The molecular weight of PAZAM and other forms of the acrylamide copolymer may range from about 5 kDa to about 1500 kDa or from about 10 kDa to about 1000 kDa, or may be, in a specific example, about 312 kDa.

In some examples, PAZAM and other forms of the acrylamide copolymer are linear polymers. In some other examples, PAZAM and other forms of the acrylamide copolymer are a lightly cross-linked polymers.

In other examples, the polymeric hydrogel 42 may be a variation of the structure (I). In one example, the acrylamide unit may be replaced with N,N-dimethylacrylamide

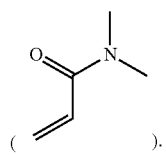

In this example, the acrylamide unit in structure (I) may be replaced with

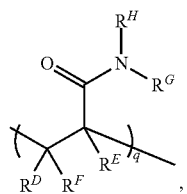

where $R^D$, $R^E$, and $R^F$ are each H or a C1-C6 alkyl, and $R^G$ and $R^H$ are each a C1-C6 alkyl (instead of H as is the case with the acrylamide). In this example, q may be an integer in the range of 1 to 100,000. In another example, the N,N-dimethylacrylamide may be used in addition to the acrylamide unit. In this example, structure (I) may include

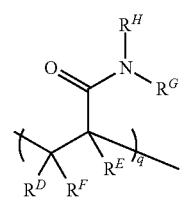

in addition to the recurring "n" and "m" features, where $R^D$, $R^E$, and $R^F$ are each H or a C1-C6 alkyl, and $R^G$ and $R^H$ are each a C1-C6 alkyl. In this example, q may be an integer in the range of 1 to 100,000.

As another example of the initial polymeric hydrogel, the recurring "n" feature in structure (I) may be replaced with a monomer including a heterocyclic azido group having structure (II):

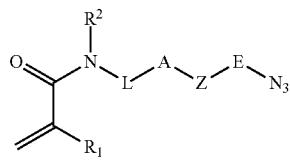

wherein $R^1$ is H or a C1-C6 alkyl; $R_2$ is H or a C1-C6 alkyl; L is a linker including a linear chain with 2 to 20 atoms selected from the group consisting of carbon, oxygen, and nitrogen and 10 optional substituents on the carbon and any nitrogen atoms in the chain; E is a linear chain including 1 to 4 atoms selected from the group consisting of carbon, oxygen and nitrogen, and optional substituents on the carbon and any nitrogen atoms in the chain; A is an N substituted amide with an H or a C1-C4 alkyl attached to the N; and Z is a nitrogen containing heterocycle. Examples of Z include 5 to 10 ring members present as a single cyclic structure or a fused structure.

As still another example, the polymeric hydrogel 42 may include a recurring unit of each of structure (III) and (IV):

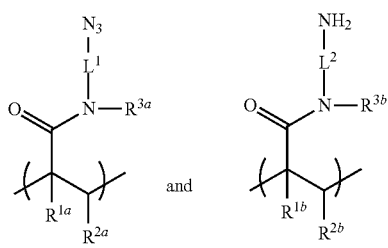

wherein each of $R^{1a}$, $R^{2a}$, $R^{1b}$ and $R^{2b}$ is independently selected from hydrogen, an optionally substituted alkyl or optionally substituted phenyl; each of $R^{3a}$ and $R^{3b}$ is independently selected from hydrogen, an optionally substituted alkyl, an optionally substituted phenyl, or an optionally substituted C7-C14 aralkyl; and each $L^1$ and $L^2$ is independently selected from an optionally substituted alkylene linker or an optionally substituted heteroalkylene linker.

It is to be understood that other molecules may be used to form the polymeric hydrogel 42, as long as they are functionalized to graft oligonucleotide primers 44, 46 thereto. Other examples of suitable polymer layers include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions. Still other examples of suitable polymeric hydrogels 42 include mixed copolymers of acrylamides and acrylates. A variety of polymer architectures containing acrylic monomers (e.g., acrylamides, acrylates etc.) may be utilized in the examples disclosed herein, such as branched polymers, including star polymers, star-shaped or star-block polymers, dendrimers, and the like. For example, the monomers (e.g., acrylamide, acrylamide containing the catalyst, etc.) may be incorporated, either randomly or in block, into the branches (arms) of a star-shaped polymer.

To introduce the polymeric hydrogel 42 into the flow channel 40, a mixture of the polymeric hydrogel 42 may be generated and then applied to the substrate 38A (having the flow channel 40 defined at least partially therein). In one example, the polymeric hydrogel 42 may be present in a mixture (e.g., with water or with ethanol and water). The mixture may then be applied to the substrate surfaces (including in the flow channel(s) 40) using spin coating, or dipping or dip coating, spray coating, or flow of the material under positive or negative pressure, or another suitable technique. These types of techniques blanketly deposit the polymeric hydrogel 42 on the substrate 38A (e.g., in the flow channel 40 and on interstitial regions 48 surrounding the flow channel 40). Other selective deposition techniques (e.g. involving a mask, controlled printing techniques, etc.) may be used to specifically deposit the polymeric hydrogel 42 in the flow channel 40 and not on the interstitial regions 48.

In some examples, the substrate surface (including the portion that is exposed in the flow channel 40) may be activated, and then the mixture (including the polymeric hydrogel 42) may be applied thereto. In one example, a silane or silane derivative (e.g., norbornene silane) may be deposited on the substrate surface using vapor deposition, spin coating, or other deposition methods. In another example, the substrate surface may be exposed to plasma ashing to generate surface-activating agent(s) (e.g., —OH groups) that can adhere to the polymeric hydrogel 42.

Depending upon the polymeric hydrogel 42, the applied mixture may be exposed to a curing process. In an example, curing may take place at a temperature ranging from room temperature (e.g., about 25° C.) to about 95° C. for a time ranging from about 1 millisecond to about several days.

In some examples, polishing may then be performed in order to remove the polymeric hydrogel 42 from the interstitial regions 48 at the perimeter of the flow channel(s) 40, while leaving the polymeric hydrogel 42 on the surface in the flow channel(s) 40 at least substantially intact.

The flow cell 36 also includes amplification primers 44, 46.

A grafting process may be performed to graft the amplification primers 44, 46 to the polymeric hydrogel 42 in the flow channel 40. In an example, the amplification primers 44, 46 can be immobilized to the polymeric hydrogel 42 by single point covalent attachment at or near the 5' end of the primers 44, 46. This attachment leaves i) an adapter-specific portion of the primers 44, 46 free to anneal to its cognate nucleic acid fragment (e.g., the P5' portion attached to the fragment 14, 14') and ii) the 3' hydroxyl group free for primer extension. Any suitable covalent attachment may be used for this purpose. Examples of terminated primers that may be used include alkyne terminated primers, which can attach to an azide moiety of the polymeric hydrogel 42. Specific examples of suitable primers 44, 46 include P5 and P7 primers used on the surface of commercial flow cells sold by Illumina Inc. for sequencing on HISEQ™, HISEQX™, MISEQ™, MISEQDX™, MINISEQ™, NEXTSEQ™, NEXTSEQDX™, NOVASEQ™, GENOME ANALYZER™, ISEQ™, and other instrument platforms.

In an example, grafting may involve flow through deposition (e.g., using a temporarily bound or permanently bonded lid), dunk coating, spray coating, puddle dispensing, or by another suitable method that will attach the primer(s) 44, 46 to the polymeric hydrogel 42 in the flow channel 42. Each of these example techniques may utilize a primer solution or mixture, which may include the primer(s) 44, 46, water, a buffer, and a catalyst. With any of the grafting methods, the primers 44, 46 react with reactive groups of polymeric hydrogel 42 in the flow channel 40 and have no affinity for the surrounding substrate 38A. As such, the primers 44, 46 selectively graft to the polymeric hydrogel 42 in the flow channel 40.

In the example shown in FIG. 5C, the flow cell 38 includes a multi-layer substrate 38B, which includes a support 52 and a patterned material 50 positioned on the support 52. The patterned material 50 defines depressions 54 separated by interstitial regions 48. The depressions 54 are located within each of the flow channel(s) 40.

In the example shown in FIG. 5C, the patterned material 50 is positioned on the support 52. It is to be understood that any material that can be selectively deposited, or deposited and patterned to form the depressions 54 and the interstitial regions 48 may be used for the patterned material 50.

As one example, an inorganic oxide may be selectively applied to the support 52 via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example, a resin may be applied to the support 52 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin (POSS)-based resin, a non-POSS epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (POSS) refers to a chemical composition that is a hybrid intermediate (e.g., $RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The polyhedral structure may be a $T_8$ structure, such as:

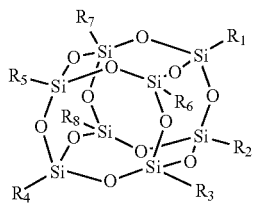

and represented by:

$T_8$

This monomeric unit typically has eight arms of functional groups $R_1$ through $R_8$.

The monomeric unit may have a cage structure with 10 silicon atoms and 10 R groups, referred to as $T_{10}$, such as:

$T_{10}$

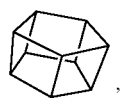

or may have a cage structure with 12 silicon atoms and 12 R groups, referred to as $T_{12}$, such as:

$T_{12}$

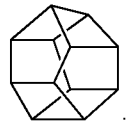

The POSS-based material may alternatively include $T_8$, $T_{14}$, or $T_{18}$ cage structures. The average cage content can be adjusted during the synthesis, and/or controlled by purification methods, and a distribution of cage sizes of the monomeric unit(s) may be used in the examples disclosed herein.

As shown in FIG. 5C, the patterned material 50 includes the depressions 54 defined therein, and interstitial regions 48 separating adjacent depressions 54. Many different layouts of the depressions 54 may be envisaged, including regular, repeating, and non-regular patterns. In an example, the depressions 54 are disposed in a hexagonal grid for close packing and improved density. Other layouts may include, for example, rectilinear (rectangular) layouts, triangular layouts, and so forth. In some examples, the layout or pattern can be an x-y format of depressions 54 that are in rows and columns. In some other examples, the layout or pattern can be a repeating arrangement of depressions 54 and/or interstitial regions 48. In still other examples, the layout or pattern can be a random arrangement of depressions 54 and/or interstitial regions 48. The pattern may include spots, pads, stripes, swirls, lines, triangles, rectangles, circles, arcs, checks, plaids, diagonals, arrows, squares, and/or crosshatches.

The layout or pattern of the depressions 54 may be characterized with respect to the density of the depressions 54 (number of depressions 54) in a defined area. For example, the depressions 54 may be present at a density of approximately 2 million per $mm^2$. The density may be tuned to different densities including, for example, a density of about 100 per $mm^2$ about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density of depressions 54 in the patterned material 50 can be between one of the lower values and one of the upper values selected from the ranges above. As examples, a high density array may be characterized as having depressions 54 separated by less than about 100 nm, a medium density array may be characterized as having depressions 54 separated by about 400 nm to about 1 μm, and a low density array may be characterized as having depressions 54 separated by greater than about 1 μm. While example densities have been provided, it is to be understood that any suitable densities may be used. The density of the depressions 54 may depend, in part, on the depth of the depressions 54. In some instances, it may be desirable for the spacing between depressions 54 to be even greater than the examples listed herein.

The layout or pattern of the depressions 54 may also or alternatively be characterized in terms of the average pitch, or the spacing from the center of the depression 54 to the center of an adjacent depression 54 (center-to-center spacing) or from the edge of one depression 54 to the edge of an adjacent depression 54 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 µm, about 0.5 µm, about 1 µm, about 5 µm, about 10 µm, about 100 µm, or more or less. The average pitch for a particular pattern of depressions 54 can be between one of the lower values and one of the upper values selected from the ranges above. In an example, the depressions 54 have a pitch (center-to-center spacing) of about 1.5 µm. While example average pitch values have been provided, it is to be understood that other average pitch values may be used.

The size of each depression 54 may be characterized by its volume, opening area, depth, and/or diameter.

Each depression 54 can have any volume that is capable of confining a fluid. The minimum or maximum volume can be selected, for example, to accommodate the throughput (e.g., multiplexity), resolution, nucleotides, or analyte reactivity expected for downstream uses of the flow cell 38. For example, the volume can be at least about $1\times10^{-3}$ µm$^3$, at least about $1\times10^{-2}$ µm$^3$, at least about 0.1 µm$^3$, at least about 1 µm$^3$, at least about 10 µm$^3$, at least about 100 µm$^3$, or more. Alternatively or additionally, the volume can be at most about $1\times10^4$ µm$^3$, at most about $1\times10^3$ µm$^3$, at most about 100 µm$^3$, at most about 10 µm$^3$, at most about 1 µm$^3$, at most about 0.1 µm$^3$, or less.

The area occupied by each depression opening can be selected based upon similar criteria as those set forth above for the volume. For example, the area for each depression opening can be at least about $1\times10^{-3}$ µm$^2$, at least about $1\times10^{-2}$ µm$^2$, at least about 0.1 µm$^2$, at least about 1 µm$^2$, at least about 10 µm$^2$, at least about 100 µm$^2$, or more. Alternatively or additionally, the area can be at most about $1\times10^3$ µm$^2$, at most about 100 µm$^2$, at most about 10 µm$^2$, at most about 1 µm$^2$, at most about 0.1 µm$^2$, at most about $1\times10^{-2}$ µm$^2$, or less. The area occupied by each depression opening can be greater than, less than or between the values specified above.

The depth of each depression 54 can large enough to house some of the polymeric hydrogel 42. In an example, the depth may be at least about 0.1 µm, at least about 0.5 µm, at least about 1 µm, at least about 10 µm, at least about 100 µm, or more. Alternatively or additionally, the depth can be at most about $1\times10^3$ µm, at most about 100 µm, at most about 10 µm, or less. In some examples, the depth is about 0.4 µm. The depth of each depression 54 can be greater than, less than or between the values specified above.

In some instances, the diameter or length and width of each depression 54 can be at least about 50 nm, at least about 0.1 µm, at least about 0.5 µm, at least about 1 µm, at least about 10 µm, at least about 100 µm, or more. Alternatively or additionally, the diameter or length and width can be at most about $1\times10^3$ µm, at most about 100 µm, at most about 10 µm, at most about 1 µm, at most about 0.5 µm, at most about 0.1 µm, or less (e.g., about 50 nm). In some examples, the diameter or length and width is about 0.4 µm. The diameter or length and width of each depression 54 can be greater than, less than or between the values specified above.

In the example shown in FIG. 5C, the polymeric hydrogel 42 is positioned within each of the depressions 54. The polymeric hydrogel 42 may be applied as described in reference to FIG. 5B, so that the polymeric hydrogel 42 is present in the depressions 54 and not present on the surrounding interstitial regions 48.

While not shown in FIG. 5A, FIG. 5B, or FIG. 5C, it is to be understood that the flow cell 36 may also include a lid attached to the substrate 38. In an example, the lid may be bonded to at least a portion of the substrate 38, e.g., at some of the interstitial regions 48. The bond that is formed between the lid and the substrate 38 may be a chemical bond, or a mechanical bond (e.g., using a fastener, etc.).

The lid may be any material that is transparent to an excitation light that is directed toward the substrate 38. As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

The lid may be bonded to the substrate 38 using any suitable technique, such as laser bonding, diffusion bonding, anodic bonding, eutectic bonding, plasma activation bonding, glass frit bonding, or others methods known in the art. In an example, a spacer layer may be used to bond the lid to the substrate 38. The spacer layer may be any material that will seal at least some of the substrate 38 and the lid together. In some examples, the spacer layer can be a radiation-absorbing material that aids in bonding of the substrate 38 and the lid.

In other examples, the flow cell 36 may also include an additional patterned or non-patterned substrate 38 attached to the substrate 38. The substrates 38 may be bonded as described herein.

Methods

The method generally includes generating a series of time-based clustering images for a plurality of contiguity preserved library fragments 14, 14' from a genome sample. Each time-based clustering image in the series is sequentially generated by introducing, to a flow cell 36, a respective sample including some of the contiguity preserved library fragments 14, 14', wherein the some of the contiguity preserved library fragments 14, 14' are attached to a solid support 16 (FIG. 1) or are attached to each other (e.g., attached fragments 34 shown in FIG. 3); initiating release of the contiguity preserved library fragments 14, 14' from the solid support 16 or from each other 34; amplifying the contiguity preserved library fragments 14, 14' to generate a plurality of respective template strands; staining the respective template strands; and imaging the respective template strands.

With the method(s) disclosed herein, the contiguity preserved library fragments 14, 14' are used in combination with sequential amplification and imaging in order to generate the series of time-based clustering images. Each time-based clustering image records the spatial location and orientation of the template strands generated using the particular sample. As such, these images can be used to identify cluster (template strand) locations, where the cluster is derived from a particular sample that was introduced to the flow cell at a particular time.

The methods may vary slightly depending upon whether the complexes 10 are introduced into the flow cell 36 or whether the attached fragments 34 are introduced into the flow cell. The various examples will now be described.

Methods Using the Complex 10 or 10'

In this example, a genome sample (e.g., sample 30) is fragmented to form a plurality of contiguity preserved fragments 14, 14', each of which is attached to a solid support 16. It is to be understood that all of the contiguity preserved fragments 14, 14' from the genome sample 30 may not be attached to the same solid support 16; but rather, contiguity preserved fragments 14, 14' associated with particular portions of the genome sample 30 may be attached to respective solids supports 16. As such, the genome sample 30 is fragmented to form a plurality of the complexes 10 or 10'. This may be accomplished as described in reference to FIG. 1, FIG. 2A through FIG. 2C, FIG. 3, or using any other contiguity preserving method that incorporates adapters 18, 22 or 18', 22 to each of the fragments 14, 14' so that they are sequencing ready fragments 12, 12'.

The complexes 10 or 10' formed using the genome sample 30 may be incorporated into a mixture. As such, each of the plurality of contiguity preserved fragments 14, 14' is also incorporated into the mixture. The liquid carrier of the mixture may be a buffer, such as Tris-HCl buffer or 0.5× saline sodium citrate (SSC) buffer.

The liquid carrier may be added to the plurality of contiguity preserved fragments 14, 14' (e.g., present in complexes 10 or 10') to initially form the mixture, and then the mixture may be diluted with additional liquid carrier to generate a predetermined number of dilution samples that are to be individually introduced to the flow cell 36 (or an individual lane 40 thereof).

The final volume of the mixture that is generated, and thus the dilution of the mixture, may be controlled in any desirable manner. In some instances, the dilution may depend upon the volume of the flow cell 36 (or, for example, each channel 40 of a multi-channel flow cell) and the desired number of samples to be introduced to the flow cell 36. In one example, the volume of the flow cell 36 (or channel 40 thereof) may be used as the limiting dilution factor. As such, in some examples, the carrier liquid may be added to dilute the mixture to the predetermined volume, where the predetermined volume is based on i) the volume of the flow cell 36 as a limiting dilution and ii) the predetermined number of dilution samples to be introduced to the flow cell 36. As an example, the flow cell 36 or one lane 40 of the flow cell 36 may have a volume of about 50 µL and the desired number of samples may be 200. In this example, the mixture may be diluted to about 10,000 µL. As another example, the flow cell 36 or one lane 40 of the flow cell 36 may have a volume of about 100 µL and the desired number of samples may be 384. In this example, the mixture may be diluted to about 38,400 µL.

The desired number of dilution samples may depend, for example, upon the volume of the flow cell 36 and the desired resolution of the individual template strands in the respective time-based clustering images. With smaller volume flow cells 38, it may be desirable to have a more dilute mixture so that each individual dilution sample to be introduced to the flow cell 36 contains fewer contiguity preserved library fragments 14, 14' (than if a less dilute mixture were used). In this type of flow cell 36, fewer contiguity preserved library fragments 14, 14' will lead to fewer template strands, which may improve the resolution of the template stands in the respective time-based clustering images. In an example, the desired number of samples may range from about 100 samples to about 1000 samples. In other examples, the desired number of dilution samples to be prepared from the mixture may be over 1000. The upper limit on the number of dilution samples may depend, in part, upon the desired time frame in which the overall method is to take place.

The mixture may then be divided into the predetermined number of dilution samples. In one example, diluted mixture may be divided so that all of the dilution samples are generated at the same time. In another example, the predetermined volume of any one dilution sample may be separated from the bulk mixture when it is time for that sample to be introduced to the flow cell 36.

FIG. 6A through FIG. 6D illustrate an example of a non-patterned flow cell 36 (e.g., as shown in FIG. 5B) from a top view during different stages of the generation of the time-based clustering images.

As shown schematically in FIG. 6A through FIG. 6D, the flow cell 36 may be introduced into a system which includes a flow cell receptacle 35; a fluidic control system 37 including delivery fluidics 39 to respectively deliver a dilution sample 56A and a stain (not shown) to a flow cell 36 positioned in the flow cell receptacle 35; an illumination system 62 positioned to illuminate the flow cell 36 positioned in the flow cell receptacle 35; a detection system 64 positioned to capture an image of the flow cell 36 positioned in the flow cell receptacle 35; and a controller 41 in operative communication with the fluidic control system 37, the illumination system 62, and the detection system 64, the controller 41 to cause the delivery fluidics 39 to introduce the dilution sample 56A to the flow cell 36 positioned in the flow cell receptacle 35; cause the delivery fluidics 39 to introduce the stain to the flow cell 36 positioned in the flow cell receptacle 35 after template strands 58A are generated in the flow cell 36 positioned in the flow cell receptacle 35 from contiguity preserved library fragments present in the dilution sample 56A; cause the illumination system 62 to illuminate the stained template strands in the flow cell 36 positioned in the flow cell receptacle 35; and cause the detection system 64 to image the illuminated, stained template strands in the flow cell 36 positioned in the flow cell receptacle 35.

When in position, the flow cell 36 is in fluid communication with the fluidic control system 39 (e.g., pumps, valves, and the like) and is in optical communication with an illumination system 62 and a detection system 64.

Figure 6A:
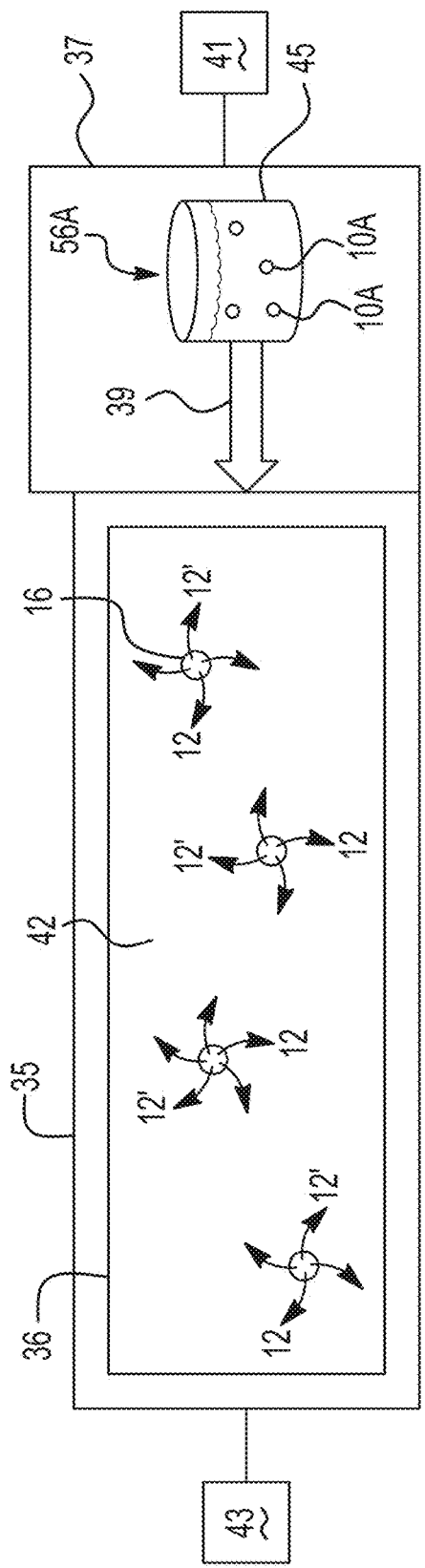

In FIG. 6A, a first of the dilution samples 56A (including some of the complexes 10 or 10', shown as 10A in FIG. 6A) is introduced into the flow cell 36. The introduction of any of the respective dilution samples 56A (or e.g., 56B in FIG. 6C) involves fluidically directing one of the dilution samples 56A, 56B to the flow cell 36. The dilution sample 56A may be introduced, e.g., in a cartridge 45, and the fluidic control system 37 may fluidically transport dilution sample 56A from the cartridge 45 to the flow channel 40 of the flow cell 36 using the delivery fluidics 39 (e.g., pumps, valves, and the like).

Given the concentration of complexes 10A in the dilution sample 56A, most, if not all, of the complexes 10A will settle onto the polymeric hydrogel 42 and any primers 44, 46 thereon (which are not shown in FIG. 6A through FIG. 6D). In some examples, the complexes 10A may settle and remain in the flow channel 40 or in the depressions 54 due to the depth of the flow channel 40 or the depressions 54. In other examples, the flow channel 40 or the depressions 54 may include a capture site that the complexes 10A adhere to.

It is to be understood that some complexes 10A may not settle, and these complexes 10A will be removed from the flow cell 36 before further processes. As such, some examples of the method then include washing away non-trapped complexes 10A from the flow cell 36. Washing may involve introducing a fluid into the flow cell 36. The flow may push any complexes 10A that have not settled and/or adhered out through an exit port of the flow cell 36.

This example of the method then includes initiating the release of the contiguity preserved library fragments 14, 14' from the respective solid supports 16 to which they are attached. In this example, the sequencing-ready nucleic acid fragments 12, 12' (including the contiguity preserved library fragments 14, 14' and the adapters 18, 22 or 18', 22 attached thereto) are released from the respective solid supports 16. In FIG. 6A, the release of the sequencing-ready nucleic acid fragments 12, 12' from the solid supports 16 is represented by the arrows pointing outward from each solid support 16.

The release of the sequencing-ready nucleic acid fragments 12, 12' may be initiated in several different ways. In one example, initiating release involves heating the flow cell 36. In this example, the system may include a heater 43. The controller 41 may cause the heater 43 to initiate release of some of the contiguity preserved library fragments 12, 12' from the solid support 16 or from each other. As an example, temperatures greater than 70° C. may be used to at least partially break the bonds, and thus initiate the release of the sequencing-ready nucleic acid fragments 12, 12'. In another example, initiating release involves introducing a cleaving agent to the flow cell 36. The fluidic control system 37 may be used to deliver the cleaving agent. The cleaving agent may initiate chemical, enzymatic, or photo-chemical release of the sequencing-ready nucleic acid fragments 12, 12' from the solid support 16. In these examples, another stimulus, such as heat or light, may trigger the cleaving agent to release the sequencing-ready nucleic acid fragments 12, 12' from the solid support 16. As one example, free biotin may be introduced as the cleaving agent, and heating to about 92° C. may be used to induce biotin-oligo release from the solid support 16.

The released sequencing-ready nucleic acid fragments 12, 12' transport from the solid support 16 and seed onto the polymeric hydrogel 42. More specifically, the amplification primers 46, 48 seed the released sequencing-ready nucleic acid fragments 12, 12' in a relatively confined manner. In an example, seeding is accomplished through hybridization between the first or second sequence of the fragment 12, 12' and a complementary one of the primers 46, 48 on the polymeric hydrogel 42 in the flow cell 36. Seeding may be performed at a suitable hybridization temperature for the fragment sequencing-ready nucleic acid fragments 12, 12' and the primer(s) 46, 48. The heater 43 may be controlled to bring the flow cell 36 to the seeding temperature.

A washing process may be performed to remove the beads.

The seeded sequencing-ready nucleic acid fragments 12, 12' can then be amplified using any suitable method, such as cluster generation. In one example of cluster generation, the released sequencing-ready nucleic acid fragments 12, 12' are copied from the hybridized primers 46, 48 by 3' extension using a high-fidelity DNA polymerase. The original sequencing-ready nucleic acid fragments 12, 12' are denatured, leaving the copies immobilized within the flow channel 40 or some of the depressions 54. Any clonal amplification process may be used. In one example, isothermal bridge amplification may be used to amplify the immobilized copies. For example, the copied templates loop over to hybridize to an adjacent, complementary primer 46, 48, and a polymerase copies the copied templates to form double stranded bridges, which are denatured to form two single stranded strands. These two strands loop over and hybridize to adjacent, complementary primers 46, 48 and are extended again to form two new double stranded loops. The process is repeated on each template copy by cycles of isothermal denaturation and amplification to create dense clonal clusters. Each cluster of double stranded bridges is denatured. In an example, the reverse strand is removed by specific base cleavage, leaving forward template polynucleotide strands. It is to be understood that clustering results in the formation of several template strands 58A in the flow channel 40 or some of the depressions 54. In some examples, the controller 41 causes the heater 43 to run a thermal cycle to amplify the seeded sequencing-ready nucleic acid fragments 12, 12'.

Figure 6B:
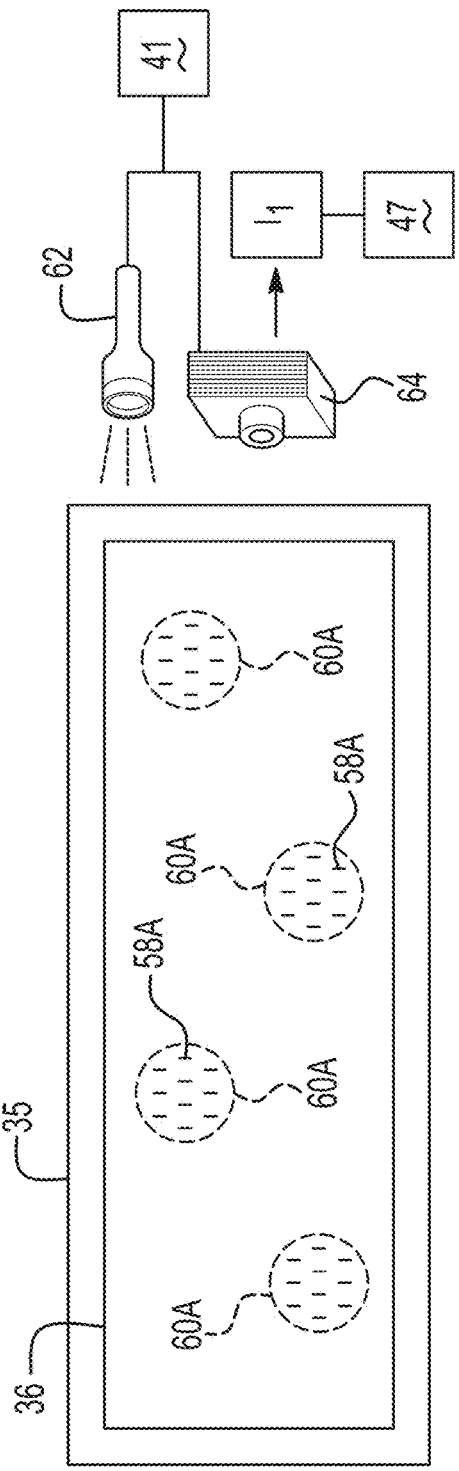

FIG. 6B illustrates clusters 60A of template strands 58A generated from the complexes 10A of the first dilution sample 56A (compartment). The clusters 60A in FIG. 6B are outlined for clarity. While FIG. 6B illustrates four clusters 60A, it is to be understood that the number of clusters 60A will depend upon the number of complexes 10A introduced in the sample 56A, as well as the number of sequencing-ready nucleic acid fragments 12, 12' released from each solid support 16. A cluster 60A is generated from each of the released sequencing-ready nucleic acid fragments 12, 12'. Moreover, the released sequencing-ready nucleic acid fragments 12, 12' may diffuse across the flow cell surface, and thus clusters 60A may be generated across the flow cell surface.

After generating the clusters 60A for the first dilution sample 56A, a stain is introduced into the flow cell 36. Any fluorescent stain that is capable of staining the template strands 58A may be used. Examples of suitable fluorescent stains include the SYBR® family of dyes from Molecular Probes, Inc. (e.g., SYBR® Green, SYBR® Gold, SYBR® Safe, etc.), ethidium bromide, propidium iodide, crystal violet, EVAGREEN® dye (from Biotium), DAPI (4',6-diamidino-2-phenylindole), or the like. The stain is introduced into the flow cell 36, e.g., from a second cartridge (not shown), allowed to incubate for a suitable time period to stain the template strands 58A, and then is flushed out of the flow cell 36.

The illumination system 62 may then be used to illuminate the stained template strands 58A in the flow cell 36. The illumination system may include a light source and a plurality of optical components Examples of light sources may include lasers, arc lamps, LEDs, or laser diodes. The optical components may be, for example, reflectors, dichroics, beam splitters, collimators, lenses, filters, wedges, prisms, mirrors, detectors, and the like. The illumination system may be operatively positioned to direct an excitation light to the flow cell surface that corresponds to the stain used.

The detection system 64 may be used to capture an image $I_1$ of the fluorescing template strands 58A. This image $I_1$ is the time-based clustering image for the dilution sample 56A because it depicts a spatial location and orientation of the template strands 58A associated with the dilution sample 56A. Any suitable camera may be used to capture an image $I_1$ of the clusters 60A on the flow cell 36.

The image $I_1$ may be electronically stored for subsequent retrieval and use. As such, some examples of the system include an electronic storage component 47 to store the image $I_1$. In the electronic record, the image $I_1$ may be linked to the dilution sample 56A. The image $I_1$ may also be assigned a temporal record. As such, some examples of the method include assigning each time-based clustering image $I_1$ in the series a temporal record of the introduction of the respective sample including the some of the contiguity preserved library fragments. The temporal record may include a time stamp indicating when the dilution sample 56A was introduced and/or imaged, a step number in an introduction and/or imaging sequence (e.g., sample 1 of 200, sample 2 of 200, . . . sample X of 200), or combinations thereof.

A wash may take place after the clusters 60A on the flow cell 36 are imaged. Water, a buffer, or another mild wash solution may be used.

The processes shown and described in reference to FIG. 6A and FIG. 6B are then repeated with a second dilution sample 56B (shown in FIG. 6C).

In FIG. 6C, the second dilution sample 56B is introduced into the flow cell 36. The complexes 10B (which may be complexes 10 or 10') settle and/or adhere to the flow cell surface.

As shown in FIG. 6C, the method then includes initiating the release of the contiguity preserved library fragments 14, 14' from the respective solid supports 16 to which they are attached. In this example, the sequencing-ready nucleic acid fragments 12, 12' (including the contiguity preserved library fragments 14, 14' and the adapters 18, 22 or 18', 22 attached thereto) are released from the respective solid supports 16.

The released sequencing-ready nucleic acid fragments 12, 12' transport from the solid support 16 and seed onto the polymeric hydrogel 42. The seeded sequencing-ready nucleic acid fragments 12, 12' can then be amplified using any suitable method, such as cluster generation. It is to be understood that this round of clustering results in the formation of several more template strands 58B in the flow channel 40 or some of the depressions 54.

FIG. 6D illustrates clusters 60B of template strands 58B generated from the respective complexes 10B of the second dilution sample 56B (compartment). The clusters 60A and 60B in FIG. 6D are outlined for clarity. While FIG. 6D illustrates three clusters 60B, it is to be understood that the number of clusters 60B will depend upon the number of complexes 10B introduced in the sample 56B, as well as the number of sequencing-ready nucleic acid fragments 12, 12' released from each solid support 16.

After generating the clusters 60B for the second dilution sample 56B, the stain is again introduced into the flow cell 36. The same stain used to stain the template strands 58A may be used to stain the template strands 58B and any subsequently generated template strands.

The illumination system 62 may then be used to illuminate the stained template strands 58A and 58B in the flow cell 36. The detection system 64 may be used to capture an image $I_2$ of the fluorescing template strands 58A and 58B in the respective clusters 60A and 60B.

The image $I_2$ may also be electronically stored for subsequent retrieval and use. In the electronic record, the image $I_2$ may be linked to the dilution sample 56B. The image $I_2$ may also be assigned a temporal record. The temporal record may include a time stamp indicating when the dilution sample 56B was imaged, a step number in a sequence (e.g., sample 2 of 200), or combinations thereof.

A wash may take place after the clusters 60A, 60B on the flow cell 36 are imaged. Water, a buffer, or another mild wash solution may be used.

The processes shown and described in reference to FIG. 6A and FIG. 6B may then be repeated, e.g., using the described system, for the number of dilution samples derived from the original mixture. Each additional image $I_3$, $I_4$, ... $I_x$ will depict new clusters 60C, 60D, ... 60X of template stands 58C, 58D, ... 58X generated with the introduction of a respective dilution sample 56C, 56D, ... 56X. All of the images $I_1$, $I_2$, ... $I_x$ obtained for the respective dilution samples 56A, 56B, ... 56X are associated with a particular mixture, and thus a particular longer nucleic acid molecule 30.

Because each sequential image $I_2$, $I_3$, $I_4$, ... $I_x$ depicts a newly formed cluster 60B, 60C, 60D, ... 60X with respect to the immediately preceding image $I_1$, $I_2$, $I_3$, ... $I_x$, image subtraction may be used to generate a resolved cluster image for each sample introduced subsequent to the first sample 56A. Some example resolved cluster images $RI_x$ are shown in FIG. 6.

Figure 7:
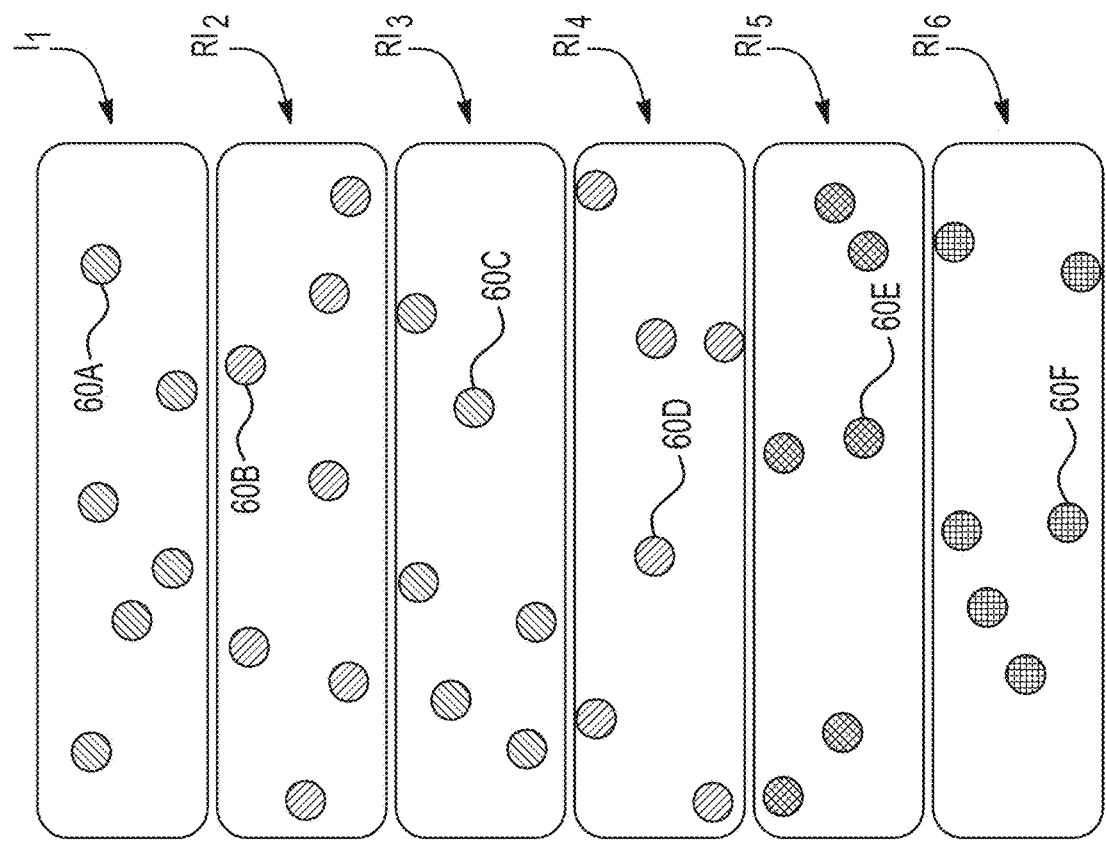
FIG. 7 is a schematic illustration of images (on the left side of FIG. 7) taken after cluster generation is performed for different samples, and resolved cluster images (on the right side of FIG. 7) generated for each of the samples.
Figure 7:
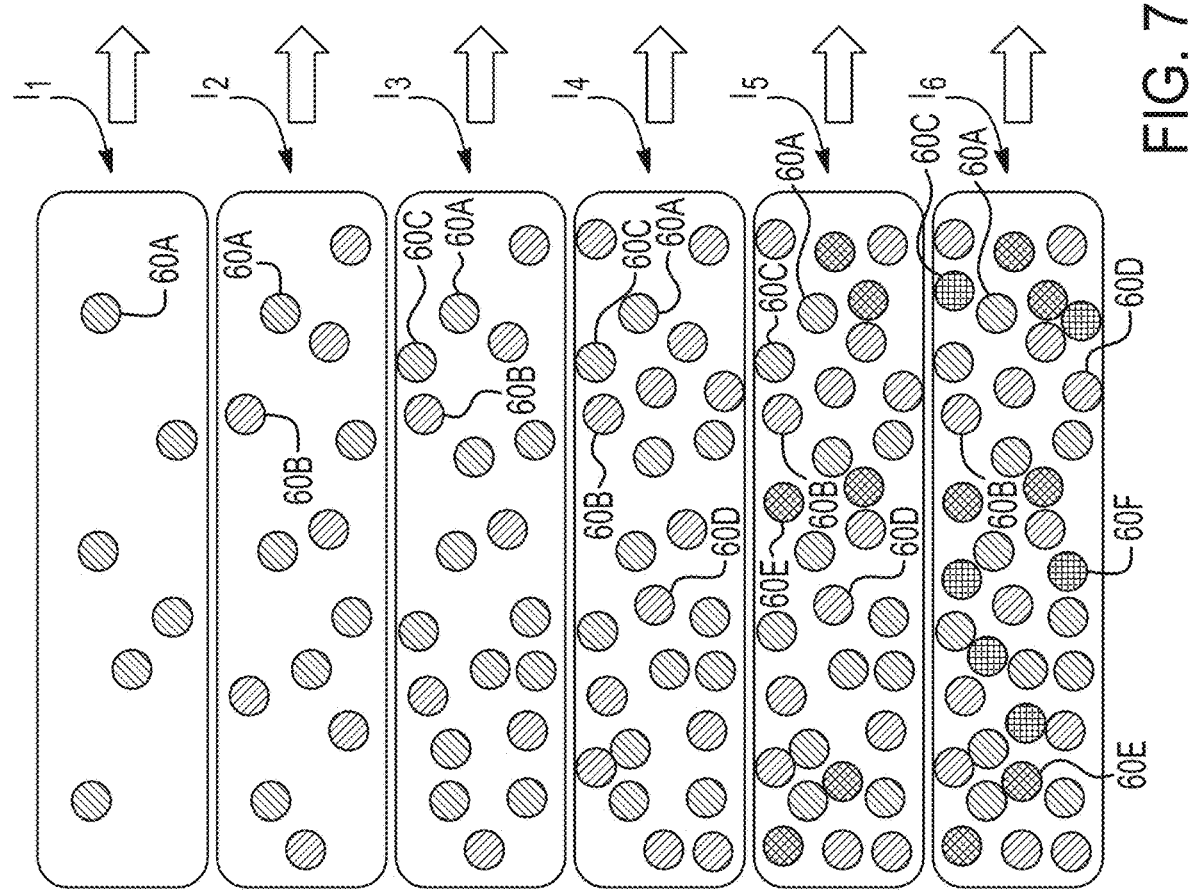

FIG. 7 depicts images $I_1$, $I_2$, $I_3$, $I_4$, $I_5$, $I_6$ taken for six different dilution samples 56A, 56B, 56C, 56D, 56E, 56F that are sequentially introduced, amplified, stained, and imaged as described in reference to FIG. 6A and FIG. 6B. As depicted, new clusters 60A, 60B, 60C, 60D, 60E, and 60F are respectively generated for each of the newly introduced and processed dilution samples 56A, 56B, 56C, 56D, 56E, 56F.

Because image $I_1$ for the first sample 56A includes clusters 60A from one sample, a resolved cluster image does not need to be generated, as the original image $I_1$ can be used for spatial identification of the clusters 60A. For each sample introduced subsequent to the first sample 56A, a resolved cluster image $RI_2$, $RI_3$, $RI_4$, $RI_5$, $RI_6$ is generated for each of the other images $I_2$, $I_3$, $I_4$, $I_5$, $I_6$. As one example, image $I_1$ (depicting template strands 58A in clusters 60A) may be subtracted from image $I_2$ (depicting template strands 58A in clusters 60A and template strands 58B in clusters 60B) to generate a resolved cluster image $RI_2$ for the second sample 56B. This resolved cluster image $RI_2$ depicts a spatial location and orientation of the template strands 58B in clusters 60B associated with the second sample 56B. For another example, image $I_1$ (depicting template strands 58A in clusters 60A) and image $I_2$ (depicting template strands 58A in clusters 60A and template strands 58B in clusters 60B) may be subtracted image $I_3$ (which depict template strands 58A in clusters 60A, template strands 58B in clusters 60B, and template strands 58C in clusters 60C) to generate a resolved cluster image $RI_3$ for a third sample, e.g., 56C. This resolved cluster image $RI_3$ depicts a spatial location and orientation of the template strands 58C in clusters 60C associated with a third sample 56C. The resolved cluster image $RI_4$, $RI_5$, and $RI_6$ may be generated in a similar manner by subtracting any of the preceding images.

It is to be understood that image subtraction may be performed for any of the $I_1$, $I_2$, $I_3$, ... $I_x$ in a series. The resulting resolved cluster image $RI_x$ for any given dilution sample 56X depicts the spatial location and orientation of the template strands 58X associated with that dilution sample 56X.

The resolved cluster images may be stored for subsequent analysis.

Methods Using the Attached Fragments 34

In this example, a genome sample is fragmented to form a plurality of contiguity preserved fragments 14, 14' that are attached to one another, e.g., as attached fragments 34. It is to be understood that all of the contiguity preserved fragments 14, 14' from the genome sample may not be attached to one another; but rather, the process shown in FIG. 4 may result in the formation of several attached fragments 34.

The attached fragments 34 formed using the genome sample may be incorporated into a mixture. As such, each of the plurality of contiguity preserved fragments 14, 14' is also incorporated into the mixture. The liquid carrier of the mixture may be a buffer, such as Tris-HCl buffer or 0.5× saline sodium citrate (SSC) buffer.

The liquid carrier may be added to a plurality of attached fragments 34 to initially form the mixture, and then the mixture may be diluted with additional liquid carrier to generate a predetermined number of dilution samples that are to be individually introduced to the flow cell 36 (or an individual lane 40 thereof).

The final volume of the mixture that is generated, and thus the dilution of the mixture, may be controlled in any desirable manner and as described herein.

The mixture may then be divided into the predetermined number of dilution samples. In one example, diluted mixture may be divided so that all of the dilution samples are generated at the same time. In another example, the predetermined volume of any one dilution sample may be separated from the bulk mixture when it is time for that sample to be introduced to the flow cell 36.

In this example method, the attached fragments 34 shown in FIG. 4 are introduced to the flow channel as part of one of the dilution samples. An example of this dilution sample 66A is depicted in FIG. 8.

Figure 8:
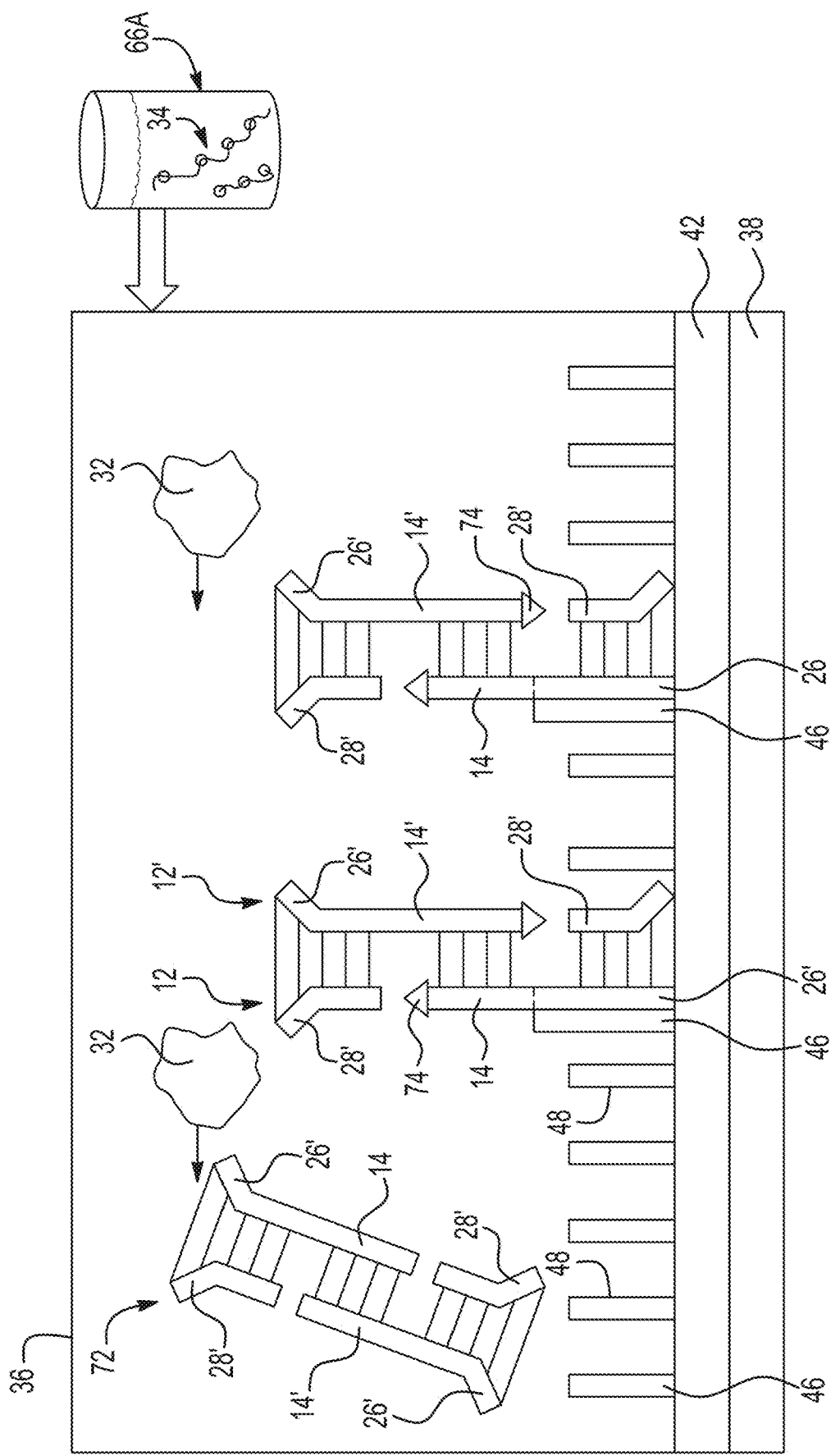
FIG. 8 is a schematic illustration of an example of a portion of a library preparation process taking place on a flow cell that utilizes the attached contiguity preserved library fragments of FIG. 4.

As shown in FIG. 8, within the flow cell 36, the transposases 32 are removed from the attached fragments 34. This may be accomplished, for example, using SDS or proteinase. The removal of the transposases 32 liberates respective contiguity preserved fragments 14, 14' (and any strands 26', 28' directly or indirectly attached thereto) from adjacent contiguity preserved fragments 14, 14'. In other words, sub-fragments 72 of the attached fragments 34 are released, and are capable of seeding onto the polymeric hydrogel 42 via the transferred strands 26'. As shown schematically in FIG. 8, the transferred strands 26' hybridize to respective and complementary primers 46 on the surface of the flow cell 36. In some instances, heat may be applied during hybridization. The application of heat may depend upon the melting temperature of the transferred strands 26'. As one example, the P5' portion of the transferred strand 26' hybridizes to the complementary P5 amplification primer 46 attached to the polymeric hydrogel 42.

A washing solution may be flowed through the flow channel of the flow cell 36 to remove the transposases 32 from the flow cell 36. An example of a suitable washing solution includes SDS, which may remove the transposase. A second wash solution, such as TRIS or a hybridization wash buffer, may be used to rinse out the flow cell 36.

Prior to amplification, this example of the method further includes introducing a second sequence portion (e.g., non-transferred strands 28') to each of the hybridized contiguity preserved library fragments 14, 14' at an end that opposed to the hybridized end. As such, in some examples of the method, each of the contiguity preserved library fragments 14, 14' includes a first sequence portion at a first end that hybridizes to a first primer sequence 46 on a surface of the flow cell 26; and prior to amplification, the method further comprises attaching a second sequence portion to each of the hybridized contiguity preserved library fragments 14, 14' at a second end that is opposed to the first end, the second sequence portion being identical to a second primer sequence 48 on the surface of the flow cell 36, so that the copy of the second sequence portion can hybridize to the second primer sequence 48.

The introduction of the second sequence portion may be performed using extension ligation. In an example, extension ligation may be initiated (as represented by the arrows 74 in FIG. 8) to join the non-transferred strands 28' to the corresponding fragments 14, 14'. In an example, extension ligation may be initiated by introducing an extension ligation mix to the flow cell 36, and heating to a suitable temperature for enzyme activity (e.g., ranging from about 37° C. to about 50° C.).

The extension ligation mix may include a ligation enzyme (e.g., DNA ligase) that catalyzes the formation of a bond between a non-transferred strand 28' and its corresponding fragment 14 or 14'. As described in reference to FIG. 4, the non-transferred strands 28' include a second sequencing primer sequence (e.g., a read 2 sequencing primer sequence) and a second sequence (P7) that is identical to at least a portion of another of the amplification primers 48 (P7) on the flow cell surface. This second sequence enables a complementary copy, e.g., P7', to be generated during amplification that can hybridize to the amplification primer 48 (P7) on the flow cell surface during clustering. As such, ligation results in the formation of sequencing ready library fragments 12, 12' attached to the flow cell surface.

The extension ligation mix may also include a blocking group that attaches to the exposed ends of the primers 46 to prevent undesired extension at these primers 46. Alternatively, primers 46 may be grafted to the surface with blocking groups (e.g., a 3' phosphate) attached thereto. In still other example, blocking groups may not be used.

As the resulting fragments 12, 12' are attached to one another, heating may be used to dissociate the fragments 12' from the fragments 12. The fragments 12' that are not hybridized to the primers 46 may be removed from the flow cell 36 with a wash.

When used, any blocked primers 46 may then be unblocked (e.g., using kinase or another suitable de-blocking agent) so that amplification can be performed. In this example, amplification may be performed using any suitable method, such as cluster generation. Cluster generation may be performed as described herein in reference to FIG. 6A. The system described in reference to FIG. 6A may be used.

Figure 9A:
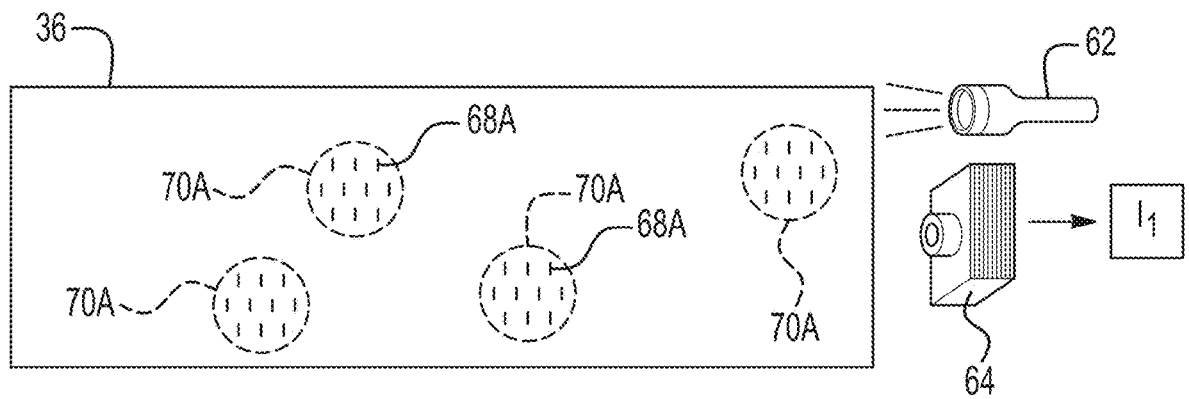
FIG. 9A through FIG. 9C are schematic views of several steps in a method for generating a series of time-based clustering images.

FIG. 9A illustrates clusters 70A of template strands 68A generated from the attached fragments 34 of the dilution sample 66A (shown in FIG. 8). The clusters 70A in FIG. 9A are outlined for clarity. While FIG. 9A illustrates four clusters 70A, it is to be understood that the number of clusters 70A will depend upon the number of attached fragments 34 introduced in the sample 66A, as well as the number of sequencing-ready nucleic acid fragments 12, 12' released from the attached fragments 34.

After generating the clusters 70A for the first dilution sample 66A, a stain is introduced into the flow cell 36 as described in reference to FIG. 6B. The stain is introduced into the flow cell 36, allowed to incubate for a suitable time period to stain the template strands 68A, and then is flushed out of the flow cell 36.

The illumination system 62 may then be used to illuminate the stained template strands 68A in the flow cell 36, and the detection system 64 may be used to capture an image $I_1$ of the fluorescing template strands 68A. This image $I_1$ is the time-based clustering image for the dilution sample 66A because it depicts a spatial location and orientation of the template strands 68A associated with the dilution sample 66A.

The image $I_1$ may be electronically stored for subsequent retrieval and use. In the electronic record, the image $I_1$ may be linked to the dilution sample 66A. The image $I_1$ may also be assigned a temporal record. The temporal record may include a time stamp indicating when the dilution sample 66A was introduced and/or imaged, a step number in an introduction and/or imaging sequence (e.g., sample 1 of 200, sample 2 of 200, . . . sample X of 200), or combinations thereof.

A wash may take place after the clusters 70A on the flow cell 36 are imaged. Water, a buffer, or another mild wash solution may be used.

Figure 9B:
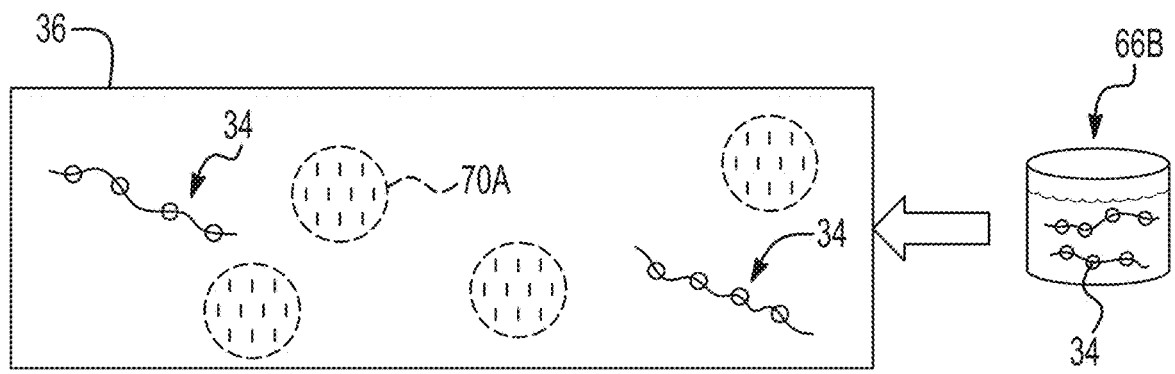

The processes shown and described in reference to FIG. 8 and FIG. 9A are then repeated with a second dilution sample 66B (shown in FIG. 9B).

In FIG. 9B, the second dilution sample 66B is introduced into the flow cell 36. The attached fragments 34 may be broken up into the sub-fragments 72 as described in reference to FIG. 8. One transferred strand 26 of at least some of the sub-fragments 72 will hybridize to complementary amplification primers 46 on the flow cell 36. Extension ligation and the other processes described in reference to FIG. 8 may then be performed, which results in sequencing-ready nucleic acid fragments 12 attached to the flow cell surface.

Cluster generation may be performed as described herein in reference to FIG. 6A.

Figure 9C:
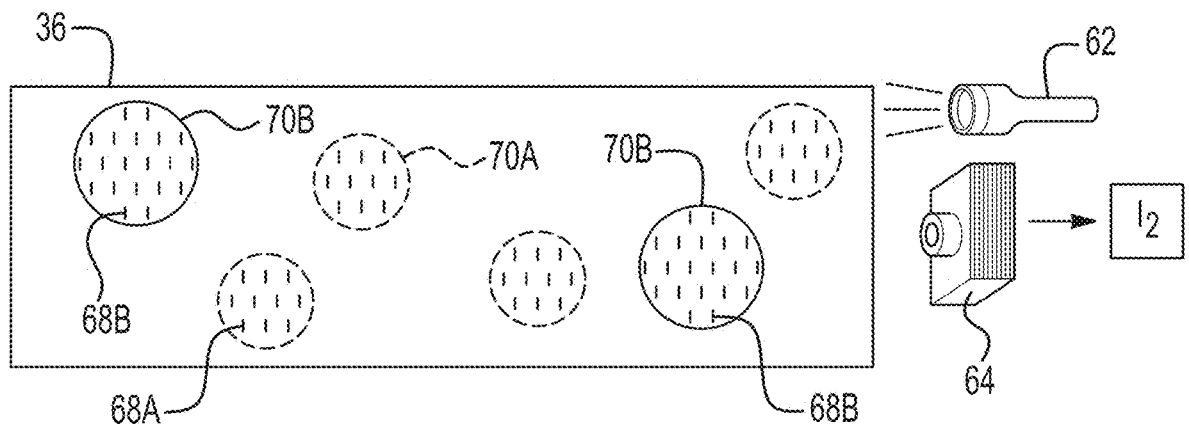

FIG. 9C illustrates clusters 70B of template strands 68B generated from the attached fragments 34 of the second dilution sample 66B. The clusters 70A and 70B in FIG. 9C are outlined for clarity. While FIG. 9C illustrates two clusters 70B, it is to be understood that the number of clusters 70B will depend upon the number of attached fragments 34 introduced in the sample 66B, as well as the number of sequencing-ready nucleic acid fragments 12, 12' released from the attached fragments 34.

After generating the clusters 70B for the second dilution sample 66B, the stain is again introduced into the flow cell 36. The same stain used to stain the template strands 68A may be used to stain the template strands 68B and any subsequently generated template strands.

The illumination system 62 may then be used to illuminate the stained template strands 68A and 68B in the flow cell 36. The detection system 64 may be used to capture an image $I_2$ of the fluorescing template strands 68A and 68B in the respective clusters 70A and 70B.

The image $I_2$ may also be electronically stored for subsequent retrieval and use. In the electronic record, the image $I_2$ may be linked to the dilution sample 66B. The image $I_2$ may also be assigned a temporal record. The temporal record may include a time stamp indicating when the dilution sample 56B was imaged and/or introduced, a step number in a sequence (e.g., sample 2 of 1000), or combinations thereof.

A wash may take place after the clusters 70A, 70B on the flow cell 36 are imaged. Water, a buffer, or another mild wash solution may be used.

The processes shown and described in reference to FIG. 9B and FIG. 9C may then be repeated for the number of dilution samples derived from the original mixture. Each additional image $I_3, I_4, \ldots I_x$ will depict new clusters 70C, 70D, . . . 70X of template stands 68C, 68D, . . . 68X generated with the introduction of a respective dilution sample 66C, 66D, . . . 66X. All of the images $I_1, I_2, \ldots 1$, obtained for the respective dilution samples 66A, 66B, . . . 66X are associated with a particular mixture, and thus a particular longer nucleic acid molecule 30.

Because each sequential image $I_2, I_3, I_4, \ldots I_x$ depicts a newly formed cluster 70B, 70C, 70D, . . . 70X with respect to the immediately preceding image $I_1, I_2, I_3, \ldots I_x$, image subtraction may be used to generate a resolved cluster image for each sample introduced subsequent to the first sample 66A. The resolved cluster images $RI_x$ may be generated as described in reference to FIG. 7.

It is to be understood that image subtraction may be performed for any of the $I_1, I_2, I_3, \ldots I_x$ in a series. The resulting resolved cluster image $RI_x$ for any given dilution sample 66X depicts the spatial location and orientation of the template strands 68X associated with that dilution sample 66X.

The resolved cluster images may be stored for subsequent analysis.

Other Methods

Rather than introducing individual dilution samples 56A, 66A, the diluted mixture may be diffused into the flow cell in predetermined volumes, and the processing on the flow cell 38 may take place as described herein to amplify, stain, and record images of the generated template strands 58X, 68X. The diffusion may be controlled so that one predetermined volume is introduced at a time.

As such, some examples of the method include generating a time-based clustering image for each of the limiting dilution samples introduced to the flow cell 36 by: controlling diffusion of the mixture into the flow cell so that one of the limiting dilution samples is introduced to the flow cell 36 at a time; initiating release of contiguity preserved library fragments 14, 14' from a solid support 16 or from each other (e.g., from attached fragments 34) in the one of the limiting dilution samples in the flow cell 36; amplifying the contiguity preserved library fragments 14, 14' to generate a plurality of respective template strands 58A, 68A; staining the respective template strands 58A, 68A; and imaging the respective template strands 58A, 68A.

Sequencing and Analysis

When all of the dilution samples from a mixture are amplified and imaged as described herein, the flow cell 36 is ready for a sequencing operation. A variety of sequencing approaches or technologies may be used, including techniques often referred to as sequencing-by-synthesis (SBS), cyclic-array sequencing, sequencing-by-ligation, pyrosequencing, and so forth.

As one example, a sequencing by synthesis (SBS) reaction may be run on a system such as the HISEQ™, HISEQX™, MISEQ™, MISEQDX™, MINISEQ™, NOVASEQ™, NEXTSEQDX™, ISEQ™ NEXTSEQ™, or other sequencer systems from Illumina (San Diego, Calif.). In SBS, extension of sequencing primers along the template strands 58A, 58B, . . . 58X is monitored to determine the sequence of nucleotides in the templates. The 3'-ends of the template strands 58A, 58B, . . . 58X and any flow cell-bound primers 46, 48 (not attached to the template strands 58A, 58B, . . . 58X) may be blocked to prevent interference with the sequencing reaction, and in particular, to prevent undesirable priming.

A sequencing primer may be introduced that hybridizes to a complementary sequence on the template strands 58A, 58B, . . . 58X. This sequencing primer renders the template strands 58A, 58B, . . . 58X ready for sequencing The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the sequencing primer in a template dependent fashion such that detection of the order and type of nucleotides added to the sequencing primer can be used to determine the sequence of the template. For example, to initiate a first SBS cycle, one or more labeled nucleotides, DNA polymerase, etc., may be delivered into/through the flow cell 36, etc., where sequencing primer extension causes a labeled nucleotide to be incorporated. This incorporation can be detected through an imaging event. During an imaging event, the illumination system 62 may provide an excitation light to the flow cell 36.

In some examples, the fluorescently labeled nucleotides can further include a reversible termination property that terminates further primer extension once a nucleotide has been added to the template. For example, a nucleotide analog having a reversible terminator moiety can be added to the template such that subsequent extension cannot occur until a deblocking agent is delivered to remove the moiety. Thus, for examples that use reversible termination, a deblocking reagent can be delivered to the flow cell 36, etc. (after detection occurs).

Wash(es) may take place between the various fluid delivery steps. The SBS cycle can then be repeated n times to extend the template by n nucleotides, thereby detecting a sequence of length n.

While SBS has been described in detail, it is to be understood that the flow cell 36 described herein may be utilized with other sequencing protocol, for genotyping, or in other chemical and/or biological applications.

The sequencing reads that are obtained during the sequencing operation can be grouped together based on the resolved cluster images $RI_2$, $RI_3$, . . . $RI_x$. The grouped sequencing reads can then be linked to a respective one of the dilution samples based on the resolved cluster images $RI_2$, $RI_3$, . . . $RI_x$. An inference can be made that the grouped and linked sequencing reads originated from the same longer nucleic acid sample 30. As such, some examples of the method include performing a sequencing operation on the flow cell 26 including the respective template strands for each of the plurality of library fragments, and grouping sequencing reads together in different groups based on the resolved clustering images RI, $RI_2$, $RI_3$, . . . $RI_x$.

To further illustrate the present disclosure, examples are given herein. It is to be understood that these examples are provided for illustrative purposes and are not to be construed as limiting the scope of the present disclosure.

EXAMPLES

Example 1

Barcode oligonucleotides (e.g., adapter 18) were attached via a biotin linker to M280 streptavidin beads (Thermofisher) to form a beadpool. A universal transposome was hybridized to the complementary sequence at the end of the oligos to form a bead-linked transposome (BLT). The BLTs were then washed in a wash buffer, resuspended in a working buffer, and accessory proteins (single strand binding protein (Thermofisher) and double stranded binding proteins (Illumina) were added.

High molecular weight NA12878 DNA (extracted from cultured cells using the Qiagen MAGATTRACT® HMW DNA extraction protocol) was added to the BLT mix and the tubes were gently inverted to mix. The tubes were then incubated at room temperature for about 15 minutes to allow the DNA to wrap around the beads. A tagmentation buffer (containing magnesium chloride and tris acetate) was then added to each tube and the samples were incubated for about 10 minutes at about 55° C. During this step, the transposome tagmented the DNA and the tagged DNA became attached to the BLTs. Following the tagmentation reaction, sodium dodecyl sulfate (SDS) was added and the samples were incubated at room temperature for about 5 minutes to denature the transposase. The tubes were then placed on a magnet and the supernatant was removed. The beads were washed with the wash buffer. Following the final wash, the beads were resuspended in a ligase mix (containing T7 ligase and its associated buffer, T7 ligase buffer from NEB). The samples were then mixed and left to incubate for about 45 minutes at room temperature. During this time, the gap in the transfer stand (where the transposome was initially hybridized) was ligated, thus physically attaching the tagged DNA to the bead. The samples were then placed on a magnet, the supernatant was removed, and the beads were again washed in the wash buffer.

The tagged beads were then split into two groups for removal of the non-transferred strands and introduction of a sample index (e.g., adapter 22). One group (comp. group) was exposed to a comparative workflow where heat was used to remove the non-transferred strands. The other group (ex. group) was exposed to an example workflow where an exonuclease was used to remove the non-transferred strands.

The comp. group was resuspended in the wash buffer were heated to about 80° C. for about 5 minutes to denature off the non-transfer strands. The tubes containing the comp. group were then placed on a magnet, the supernatant was removed, and the beads were washed. The sample index, diluted in the wash buffer, was then added to the beads of the comp. group, and this mixture was incubated at about 80° C. for about 1 minute, followed by a slow temperature ramp down.

The ex. group was suspended in a T7 exonuclease mix (containing T7 exonuclease and NEB Buffer 4), and was allowed to incubate at room temperature for about 10 minutes. The 5' to 3' exonuclease activity of the T7 exonuclease digested the non-transferred strands. The tubes containing ex. group were then placed on a magnet, the supernatant was removed, and the beads were washed. The sample index, diluted in the wash buffer, was then added to the beads of the ex. group, and this mixture was incubated at about 55° C. for about 5 minutes to allow the sample index to anneal.

The tubes respectively containing comp. group and the ex. group were placed on a magnet and the supernatant was removed. An extension ligation mix was added, and the samples were incubated for about 5 minutes at about 37° C. The tubes were again placed on a magnet, the supernatant was removed, and the beads of the comp. group and the ex. group were washed in the wash buffer. Following the final wash, the beads were resuspended in the wash buffer.

Some beads of the comp. group and some beads of the ex. group were subsampled and used in a PCR reaction. In addition to the respective beads, each PCR mix consisted of Illumina PCR mix EPM, and P5 and P7 oligos. Each sample was amplified using PCR.

Following PCR, a subsample of the PCR supernatant of each of the comp. group and the ex. group was transferred to a fresh tube and a 0.50×-0.62× size selection (solid phase reversible immobilization, SPRI) was performed using sample purification beads. The resulting libraries were eluted in a resuspension buffer. These libraries were sequenced on individual HISEQ™ 2500 Rapid flow cells (using a standard 2×101 cycle read length). Following Fastq generation, the samples were aligned to the human genome (hg38) and the data imported into IGV.

Figure 10:
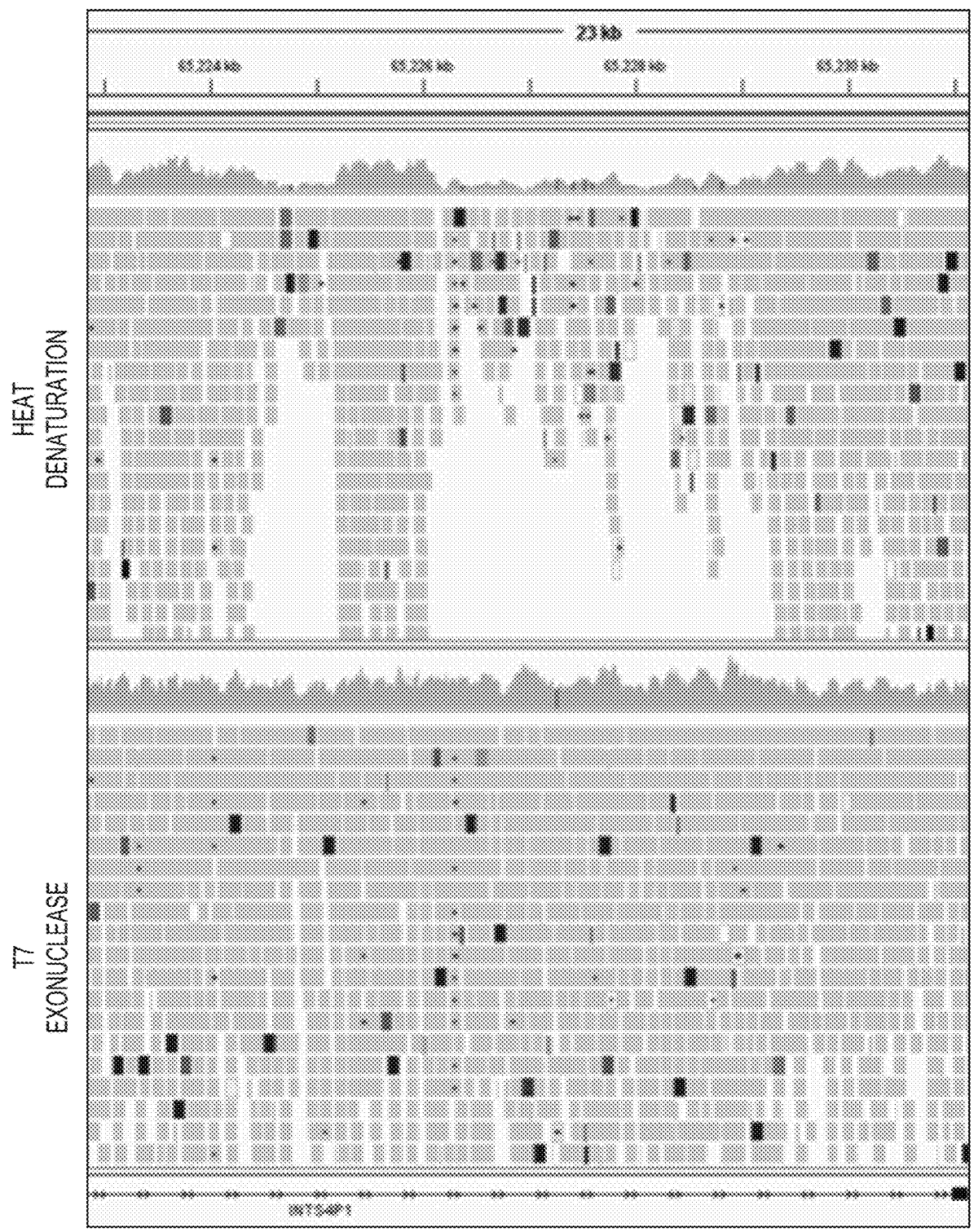
FIG. 10 is an originally colored screenshot, reproduced in black and white, from an Integrative Genomics Viewer (IGV) browser depicting results for an AT rich region of the INTS4P1 gene when a non-transferred strand was removed using heat denaturation and when a non-transferred strand was removed using T7 exonuclease conditions.

FIG. 10 shows coverage obtained, using the library from each of the comp. group (labeled heat denaturation) and the ex. group (labeled T7 exonuclease), for an AT rich region of the human genome that is known to be negatively affected by high temperature steps in the library preparation protocol. The results for the comp. group library fragments whose non-transferred strands were removed via heat denaturation are shown at the top of FIG. 10, and the results for the ex. group library fragments whose non-transferred strands were removed via exonuclease digestion are shown at the bottom of FIG. 10. As illustrated, there was full coverage in the AT rich region for the ex. group library fragments, while there was only partial coverage in the same region for the comp. group library fragments. These results indicate that the use of the enzymatic digestion method disclosed herein increases library coverage and improves sequencing over AT rich regions of the genome when compared to heat denaturation.

Example 2

Complexes were prepared as described in the method of FIG. 2A through FIG. 2C (multi-step ligation and digestion) and in the method of FIG. 3 (one pot ligation and digestion).

BLT generation, DNA binding, tagmentation, and exposure to SDS were performed as described in Example 1. Following the removal of the transposase and the wash associated therewith, the tagged beads were then split into two groups for removal of the non-transferred strands via multi-step ligation and digestion (referred to as ex. group 2) or via one pot ligation and digestion (referred to as ex. group 3).

Ex. group 2 was resuspended in an *E. Coli* DNA ligase mix including *E. Coli* DNA ligase and its associated buffer, both from NEB. The ex. group 2 samples were then mixed and incubated for about 15 minutes at about 16° C. The tubes containing the ex. group 2 samples were then placed on a magnet, the supernatant was removed, and the ex. group 2 beads were washed in the wash buffer. After the wash, the ex. group 2 beads were resuspended in a mix containing T7 Exonuclease and NEB Buffer 4 and were incubated at about 25° C. for about 10 minutes.

Ex. group 3 was resuspended in a combined ligase and exonuclease mix including *E. Coli* DNA ligase, T7 exonuclease, NAD$^+$, and a CUTSMART™ buffer (from NEB) at about 25° C. for about 15 minutes.

The tubes containing ex. group 2 and ex. group 3 were then placed on a magnet, the supernatant was removed, and the respective beads were washed. The sample index, diluted in the wash buffer, was then added to the beads of each ex. group, and these mixtures were incubated at about 55° C. for about 5 minutes to allow the sample index to anneal.

The tubes respectively containing ex. group 2 and the ex. group 3 were placed on a magnet and the supernatant was removed. An extension ligation mix was added, and the samples were incubated for about 5 minutes at about 37° C. The tubes were again placed on a magnet, the supernatant was removed, and the beads of the comp. group and the ex. group were washed in the wash buffer. Following the final wash, the beads were resuspended in the wash buffer.

Some beads of the ex. group 2 and some beads of the ex. group 3 were subsampled and used in a PCR reaction. In addition to the respective beads, each PCR mix consisted of Illumina PCR mix EPM, and P5 and P7 oligos. Each sample was amplified using PCR.

Following PCR, a subsample of the PCR supernatant of each of the ex. group 2 and the ex. group 3 was transferred to a fresh tube. Sample purification beads were added and a 2.5×SPRI was performed with the resulting library being eluted in a resuspension buffer. The cleaned-up libraries were then run on a Bioanalyzer 2100 High Sensitivity chip and the trace in FIG. 11 was obtained. The results show that size profiles and yields of the libraries were comparable for the multi-step ligation and digestion and for the one pot ligation and digestion. These results indicate that the combined reagent formulation did not deleteriously affect ligation and did not result in digestion of the fragment or transferred strand.

The example bead bound library fragments (complexes) obtained using the library preparation methods described in Examples 1 and 2 may be divided into subsamples and diluted to form a plurality of dilution samples as described herein. The method described in reference to FIG. 6A through FIG. 6D (including clustering, staining, and imaging) may then be performed with each of the dilution samples to generate a series of time-based clustering images. When all of the dilution samples are amplified and imaged, the flow cell is ready for a sequencing operation. The library preparation techniques and time-based imaging techniques disclosed herein may be used together to efficiently and reliably reconstitute a long DNA fragment.

Additional Notes

Furthermore, it is to be understood that the ranges provided herein include the stated range and any value or sub-range within the stated range, as if they were explicitly recited. For example, a range represented by from about 2 mm to about 300 mm, should be interpreted to include not only the explicitly recited limits of from about 2 mm to about 300 mm, but also to include individual values, such as about 15 mm, 22.5 mm, 245 mm, etc., and sub-ranges, such as from about 20 mm to about 225 mm, etc.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

While several examples have been described in detail, it is to be understood that the disclosed examples may be modified. Therefore, the foregoing description is to be considered non-limiting.

What is claimed is:

1. A method, comprising:
   generating a series of time-based clustering images for a plurality of contiguity-preserved library fragments from a genome sample, wherein each time-based clustering image in the series is sequentially generated by:
      introducing, to a flow cell, a respective sample including some of the contiguity-preserved library fragments, wherein the some of the contiguity-preserved library fragments are attached to a solid support or are attached to each other;
      initiating release of the some of the contiguity-preserved library fragments from the solid support or from each other;
      amplifying the some of the contiguity-preserved library fragments to generate a plurality of respective template strands;
      staining the respective template strands; and
      imaging the respective template strands.

2. The method as defined in claim 1, further comprising assigning each time-based clustering image in the series a temporal record of the introduction of the respective sample including the some of the contiguity-preserved library fragments.

3. The method as defined in claim 2, wherein the temporal record is a time stamp or a step number in a sequence.

4. The method as defined in claim 1, further comprising using image subtraction to generate a resolved clustering image for each of the respective samples, wherein each resolved clustering image records a spatial location and orientation of the respective template strands associated with a different one of the samples.

5. The method as defined in claim 4, further comprising storing the resolved clustering images.

6. The method as defined in claim 4, further comprising:
performing a sequencing operation on the flow cell including the respective template strands for each of the plurality of library fragments; and
grouping sequencing reads together in different groups based on the resolved clustering images.

7. The method as defined in claim 6, further comprising linking the different groups to each of the different one of the samples based on the resolved clustering images.

8. The method as defined in claim 1, wherein:
prior to generating the series of time-based clustering images, the method further comprises:
adding a liquid carrier to the plurality of contiguity-preserved library fragments to form a mixture; and
diluting the mixture with the liquid carrier to generate a predetermined number of dilution samples to be introduced to the flow cell; and
the introduction of the respective sample involves fluidically directing one of the dilution samples to the flow cell.

9. The method as defined in claim 8, wherein the mixture including the plurality of contiguity-preserved library fragments is diluted to a predetermined volume based on i) a volume of the flow cell as a limiting dilution and ii) the predetermined number of dilution samples.

10. The method as defined in claim 1, wherein:
each contiguity-preserved library fragment is attached to the solid support; and
the release involves heating.

11. The method as defined in claim 1, wherein:
each of the contiguity-preserved library fragments includes a first sequence portion at a first end that hybridizes to a first primer sequence on a surface of the flow cell; and
prior to amplification, the method further comprises attaching a second sequence portion to each of the hybridized contiguity-preserved library fragments at a second end that is opposed to the first end, the second sequence portion being identical to a second primer sequence on the surface of the flow cell.

12. The method as defined in claim 1, wherein:
each contiguity-preserved library fragment is attached to the solid support;
the solid support has a plurality of adapters attached thereto; and
the method further comprises preparing the contiguity-preserved library fragment attached to the solid support by:
tagmenting the genome sample in the presence of the solid support and a plurality of L-adapters, each L-adapter including a transferred strand and a non-transferred strand, thereby generating a plurality of sample fragments, whereby a respective transferred strand is incorporated to a 5'-end of each sample fragment and a respective non-transferred strand is hybridized to a portion of each adapter;
ligating the respective transferred strands to a respective one of the plurality of adapters;
digesting the non-transferred strand using a 5'-3' exonuclease; and
attaching a partial Y-adapter to each of the transferred strands.

13. The method as defined in claim 12, wherein ligating and digesting occur in a single, one pot protocol.

14. A method, comprising:
preparing a mixture including a plurality of contiguity-preserved library fragments of a genome sample, the plurality of contiguity-preserved library fragments being attached to solid supports or being attached to each other;
diluting the mixture to generate a predetermined number of dilution samples to be introduced to a flow cell; and
generating a clustering image for one of the contiguity-preserved library fragments by:
introducing a first of the dilution samples including some of the contiguity-preserved library fragments to the flow cell;
initiating release of the some of the contiguity-preserved library fragments from the solid support or from each other;
amplifying the some of the contiguity-preserved library fragments to generate a plurality of template strands;
staining the plurality of template strands; and
imaging the plurality of template strands.

15. The method as defined in claim 14, wherein the mixture is diluted to a predetermined volume based on i) a volume of the flow cell as a limiting dilution and ii) the predetermined number of dilution samples to be introduced to the flow cell.

16. The method as defined in claim 14, wherein:
the clustering image is a first time-based clustering image in a series of time-based clustering images for the plurality of contiguity-preserved library fragments;
each time-based clustering image in the series is sequentially generated; and
the method further comprises:
generating a second time-based clustering image for some other of the contiguity-preserved library fragments by:
introducing a second of the dilution samples including the some other of the contiguity-preserved library fragments to the flow cell;
initiating release of the some other of the contiguity-preserved library fragments from the solid support or from each other;
amplifying the some other of the contiguity-preserved library fragments to generate a second plurality of template strands;
staining the second plurality of template strands; and
imaging the second plurality of template strands.

17. The method as defined in claim 16, further comprising generating a predetermined number of time-based clustering images for a predetermined number of the contiguity-preserved library fragments by repeating the introducing, the initiating release, the amplifying, the staining, and the imaging with each other of the predetermined number of dilution samples.

18. The method as defined in claim 17, further comprising assigning each of the predetermined number of time-based clustering images a temporal record of the introduction of the respective dilution sample.

19. The method as defined in claim 18, wherein the temporal record is a time stamp or a step number in a sequence.

20. The method as defined in claim 17, further comprising using image subtraction to generate a resolved cluster image for each of the dilution samples introduced to the flow cell, wherein each resolved cluster image records a spatial location and orientation of the plurality of template strands associated with a different one of the dilution samples.

21. The method as defined in claim 14, wherein:
each contiguity-preserved library fragment is attached to the solid support;

the solid support has a plurality of adapters attached thereto; and the method further comprises preparing the contiguity-preserved library fragment attached to the solid support by:

tagmenting the genome sample in the presence of the solid support and a plurality of L-adapters, each L-adapter including a transferred strand and a non-transferred strand, thereby generating a plurality of sample fragments, whereby a respective transferred strand is incorporated to a 5'-end of each sample fragment and a respective non-transferred strand is hybridized to a portion of each adapter;

ligating the respective transferred strands to a respective one of the plurality of adapters;

digesting the non-transferred strand using a 5'-3' exonuclease; and attaching a partial Y-adapter to each of the transferred strands.

22. The method as defined in claim 21, wherein ligating and digesting occur in a single, one pot protocol.

23. A system, comprising:
a flow cell receptacle;
a fluidic control system including delivery fluidics configured to respectively deliver a dilution sample and a stain to a flow cell positioned in the flow cell receptacle;
an illumination system positioned to and configured to illuminate the flow cell positioned in the flow cell receptacle;
a detection system positioned to and configured to capture an image of the flow cell positioned in the flow cell receptacle;
a data storage device storing instructions; and
a controller in operative communication with the data storage device, the fluidic control system, illumination system, and the detection system, the controller configured to execute the instructions to:

cause the delivery fluidics to introduce the dilution sample to the flow cell positioned in the flow cell receptacle;

cause the delivery fluidics to introduce the stain to the flow cell positioned in the flow cell receptacle after template strands are generated in the flow cell positioned in the flow cell receptacle from contiguity-preserved library fragments present in the dilution sample;

cause the illumination system to illuminate the stained template strands in the flow cell positioned in the flow cell receptacle; and cause the detection system to image the illuminated, stained template strands in the flow cell positioned in the flow cell receptacle.

24. The system as defined in claim 23, wherein the flow cell receptacle is part of a sequencer that includes a heater, wherein the controller is further configured to execute the instructions to:

cause the heater to initiate release of the some of the contiguity-preserved library fragments from a solid support or from each other;

cause the heater to run a thermal cycle to amplify the some of the contiguity-preserved library fragments to generate the template strands.

25. The system as defined in claim 23, further comprising:
a first cartridge containing the dilution sample; and
a second cartridge containing the stain.

26. The system as defined in claim 23, further comprising an electronic storage component configured to store the image.

27. The system as defined in claim 23, wherein the image is a time-based clustering image in a series of time-based clustering images for a plurality of contiguity-preserved library fragments from a genome sample, wherein each time-based clustering image in the series is sequentially generated.

* * * * *